(12) United States Patent
Arai et al.

(10) Patent No.: US 6,493,415 B1
(45) Date of Patent: Dec. 10, 2002

(54) X-RAY COMPUTED TOMOGRAPHY METHOD AND APPARATUS

(75) Inventors: Yoshinori Arai, Tokyo (JP); Masakazu Suzuki, Kyoto (JP)

(73) Assignees: Nihon University, Tokyo (JP); J. Morita Manufacturing Corporation, Kyoto (JP)

( * ) Notice: Subject to any disclaimer, the term of this patent is extended or adjusted under 35 U.S.C. 154(b) by 0 days.

(21) Appl. No.: 09/937,245

(22) PCT Filed: Mar. 27, 2000

(86) PCT No.: PCT/JP00/01844

§ 371 (c)(1),
(2), (4) Date: Dec. 28, 2001

(87) PCT Pub. No.: WO00/57789

PCT Pub. Date: Oct. 5, 2000

(30) Foreign Application Priority Data

Mar. 25, 1999 (JP) .............................................. 11-81518

(51) Int. Cl.⁷ .............................................. H05G 1/60

(52) U.S. Cl. ................................. 378/4; 378/38; 378/39
(58) Field of Search ............................... 378/38, 39, 4, 378/901

(56) References Cited

U.S. PATENT DOCUMENTS 5,293,312 A  *  3/1994  Waggener ..................... 378/14
6,289,074 B1 *  9/2001  Arai et al. ..................... 378/38

* cited by examiner

Primary Examiner—David V. Bruce
Assistant Examiner—Pamela R. Hobden
(74) Attorney, Agent, or Firm—Koda & Androlia

(57) ABSTRACT

An X-ray computed tomography method and apparatus for obtaining a panoramic X-ray image seen from a direction of a projection line γ (γ') of a curved sectional area SA by expanding calculation results of three-dimensional distribution information of X-ray absorption coefficient on the projection line γ (γ') intersecting at a specified angle β (β') for any regions α of the panoramic sectional image layer SB on a two-dimensional plane based on the three dimensional distribution information of X-ray absorption coefficient of the curved sectional area SA obtained by a X-ray CT.

29 Claims, 33 Drawing Sheets

*Fig.26a*
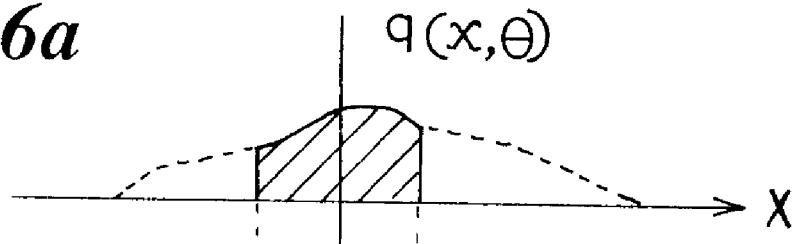
*Fig.26b*
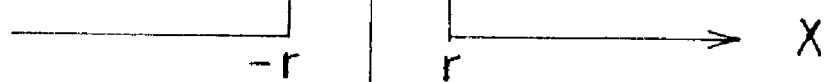
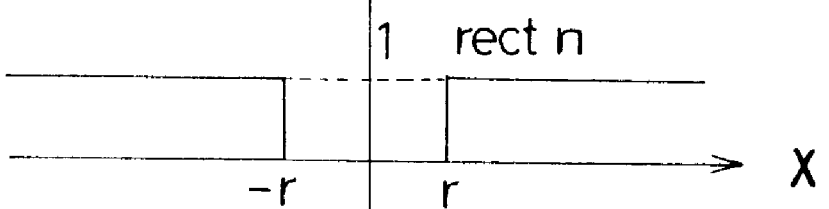
*Fig.26c* arithmetical expressions
of the basic principle of an X-ray CT $X = x\cos\theta + y\sin\theta, \quad Y = -x\sin\theta + y\cos\theta$ ⋯ coordinate conversion formula $p(X,\theta) = \int_{-\infty}^{\infty} f(x,y) dY$ ⋯ (formula 1)

$q(X,\theta) = \frac{1}{2} \int_{-\infty}^{\infty} p(X',\theta) h(X-X') dX'$ ⋯ (formula 2)

$f(x,y) = \frac{1}{2\pi} \int_{0}^{2\pi} q(x,\theta) d\theta$ ⋯ (formula 3)

$f(x,y) = \frac{1}{2\pi} \int_{0}^{2\pi} \frac{1}{2} \int_{-\infty}^{\infty} p(X',\theta) h(X-X') dX' d\theta$ ⋯ (formula 4)

*Fig.31* arithmetical expressions of an X-ray CT
of the present invention (the beam width = 2r)

if $|X| \leq r$  $\text{rect}_s(X)=1$  else $|X|>r$  $\text{rect}_s(X)=0$ if $|X| \leq r$  $\text{rect}_n(X)=0$  else $|X|>r$  $\text{rect}_n(X)=1$ ... (formula 5)

$\text{rect}_s(X)+\text{rect}_n(X)=1$ $$q(X,\theta)=\frac{1}{2}\int_{-\infty}^{\infty}\{\text{rect}_s(X')+\text{rect}_n(X')\}p(X',\theta)h(X-X')dX' \quad \cdots \text{(formula 6)}$$

$$=\frac{1}{2}\int_{-\infty}^{\infty}\text{rect}_s(X')p(X',\theta)h(X-X')dX'+\frac{1}{2}\int_{-\infty}^{\infty}\text{rect}_n(X')p(X',\theta)h(X-X')dX'$$

$\cdots$ (formula 6-1)

$=q_s(X,\theta)+q_n(X,\theta)$    $\cdots$ (formula 7)

$f(x,y)=\frac{1}{2\pi}\int_0^{2\pi}\{q_s(X,\theta)+q_n(X,\theta)\}d\theta$ $f(x,y)=f_s(x,y)+f_n(x,y)$ $f_s(x,y)=f(x,y)-f_n(x,y)$    $\cdots$ (formula 8)

$r^2 \geq x^2+y^2$

*Fig.32* arithmetical of an X-ray CT for producing a panorama image
of the present invention $$\text{if}|X| \leq r \quad \text{rect}_s(X)=1 \quad \text{else}|X|>r \quad \text{rect}_s(X)=0$$

$$\text{if}|X| \leq r \quad \text{rect}_n(X)=0 \quad \text{else}|X|>r \quad \text{rect}_n(X)=1 \quad \cdots \text{(formula 9)}$$

$$\text{rect}_s(X)+\text{rect}_n(X)=1$$

$$q(X,\theta)=\frac{1}{2}\int_{-\infty}^{\infty}\{\text{rect}_s(X')+\text{rect}_n(X')\}p(X',\theta)h(X-X')dX' \quad \cdots \text{(formula 10)}$$

$$=\frac{1}{2}\int_{-\infty}^{\infty}\text{rect}_s(X')p(X',\theta)h(X-X')dX'+\frac{1}{2}\int_{-\infty}^{\infty}\text{rect}_n(X')p(X',\theta)h(X-X')dX'$$

$$=q_s(X,\theta)+q_n(X,\theta)$$

$$=q_s(X,\theta) \quad \because q_n(X,\theta)=0 \quad \cdots \text{(formula 11)}$$

$$f_s(x,y)=\frac{1}{\psi(x,y)-\phi(x,y)}\int_{\phi(x,y)}^{\psi(x,y)}q_s(X,\theta)d\theta \quad \cdots \text{(formula 12)}$$

*Fig.33*

X-RAY COMPUTED TOMOGRAPHY METHOD AND APPARATUS

BACKGROUND OF THE INVENTION

1. Field of the Invention

The present invention relates to an X-ray computed tomography (CT) method and apparatus for obtaining panoramic X-ray images of an object to be examined seen from an optional direction by radiating a conical X-ray beam on a part of the object to be examined.

2. Prior Art

A method of obtaining a panoramic X-ray image known as X-ray computer tomography (CT) has been widely used in medical practice as for diagnosis. This method involves radiating X-rays on the object from all around, followed by analyzing a three-dimensional absorption coefficient distribution information, namely a three-dimensional distribution information of an X-ray absorption coefficient, on the X-rayed object from the projection data by the Radon theory as widely known, thereby obtaining a sectional image of object.

The prior art X-ray CT is a technique in which a fan-shaped X-ray beam relatively wide in the direction of rotation and thin is radiated on the object from around at a depth and this is repeated at different depths.

Accordingly, in the event that only a part inside the object is to be put to tomography examination, the fan-shaped wide X-ray beam is radiated over the whole object to obtain a three-dimensional distribution information of an X-ray absorption coefficient from which a three-dimensional distribution information of an X-ray absorption coefficient on that part or region is taken out for analysis. That is, the object is exposed to a substantial dose of the X-ray beam. In addition, it takes long to radiograph and analyze the test data. Accordingly in the light of high dose of radiation, the CT examination is limited to some once a year.

The applicant of the present invention proposes an X-ray computer tomography (CT) method and apparatus for solving the problem of exposed dose of the X-ray beam, namely by radiating conical X-ray beams of a small section area onto a local region, the object to be examined, only once, the three-dimensional distribution information of an X-ray absorption coefficient of the local region is calculated out.

FIG. 24a is a plane view conceptually showing the area of the three-dimensional distribution information of an X-ray absorption coefficient obtained by the X-ray CT apparatus, FIG. 24b is a partial plane view for conceptually showing the method for producing panoramic X-ray images from the three-dimensional distribution information of an X-ray absorption coefficient and FIG. 24c is a partial view of the panoramic X-ray image produced by this method.

In FIG. 24a, S is a dental arch and SA is a curved sectional area along the dental arch S and is covered by oblique lines. According to the X-ray CT apparatus, a distribution information of an X-ray absorption coefficient is obtained for the curved sectional area SA, which is an object to be examined. In this area SA, if a region is designated, the three-dimensional distributed information of an X-ray absorption coefficient at the region can be obtained. SB is a panoramic image layer of the curved sectional area SA. Lc is a normal line to the panoramic image layer SB. In FIG. 24b, H1 and H2 conceptually show foreign objects existing inside of a part of the dental arch S.

The X-ray CT apparatus enables the production of normal panoramic X-ray images as such shown in FIG. 24c by processing the three-dimensional distribution information of an X-ray absorption coefficient on the normal line Lc to the panoramic image layer SB shown in FIG. 24b. It also enables the production of sectional images of selected teeth, wherein the X-ray exposed dose is decreased to about 1 to 5% of that in case of using conventional systems.

But the panoramic X-ray images produced by the above mentioned method has one problem: as the production method of panoramic X-ray images is limited to the method shown in FIG. 24b, if there are any foreign materials H1 and H2 in the direction of a normal line LC, they are overlapped in the obtained panoramic X-ray image shown in FIG. 24c and cannot be distinguished. In addition, how a tooth is overlapped with another is sometimes invisible on a panoramic view produced from one direction.

The applicant of the present invention has proposed a panoramic X-ray picturing apparatus applicable to various dental arches in a Japanese patent application laid on unexamined under No. S60-103942. With this apparatus, the loci of the rotation of panoramic X-ray radiation can be adjusted depending on male, female or children examinees. The direction of normal lines to the dental arches is changeable depending on the size of the dental arch, and the problem derived from the fixed normal line mentioned above has been solved with that apparatus.

This apparatus, however, requires the loci of the rotation of panoramic X-ray radiation to be changed in order to obtain different panoramic X-ray images, so that the setting condition should be set before picturing. Another problem is that as this apparatus was not made for a computer tomography but for a conventional picturing of sectional images, it also requires the rotating center of the rotary arm to be moved along the specified loci during picturing, which needs a complex driving mechanism.

The applicant of this invention has also introduced in a Japanese patent application laid on unexamined under No. H4-144549 a digital panoramic X-ray picturing apparatus with which panoramic X-ray images of sectional image layers obliquely crossing the curved sectional image layers are produced.

This apparatus enabled the production of panoramic X-ray images seen from the oblique direction of the dental arch. It uses a frame image comprising the projection images and obtains partial images by shifting at a predetermined distance in accordance with the direction of the image shifting in a specific time period. Then the partial images are added to obtain a panoramic X-ray image seen from obliquely.

With this apparatus, however, the data from the obtained projection images is recalculated only after a digital processing and does not utilize the CT method computing a three-dimensional distribution information of an X-ray absorption coefficient by means of backprojection processing, so that the overlapped foreign materials H1 and H2 can not be distinguished.

SUMMARY OF THE INVENTION

The present invention has been proposed to solve the above-mentioned problems. According to which, a projection image taken by one X-ray picturing can be effectively utilized with all sorts of merits of X-ray computed tomography method and apparatus using a conical X-ray beam, and a panoramic X-ray image of one panoramic sectional image layer seen from an optional direction can be further gained.

The present invention has been developed to solve those problems as a result of intensive researches by the inventors and following (1)–(11) propose its method and (12)–(29) propose its apparatus.

In the X-ray CT of the present invention, a dental arch being an object to be examined is considered as a curved sectional area, an X-ray projection image is obtained for the curved sectional area by local radiation, the obtained X-ray projection image is processed by a backprojection method, and a three-dimensional distribution information of an X-ray absorption coefficient of the curved sectional area is calculated. Then the three-dimensional distribution information of an X-ray absorption coefficient is reconstructed by several methods, namely the three-dimensional distribution information of an X-ray absorption coefficient on a projection line intersecting a normal line of an area at an optional angle is calculated for the area on a panoramic image layer of the curved sectional area, the calculated result is expanded on a two-dimensional plane, and a panoramic X-ray image wherein the curved sectional area is seen from an optional projection line can be produced.

(1) An X-ray computed tomography method of the present invention is comprised of: sequentially obtaining on a two-dimensional X-ray image sensor an X-ray projection image information of a curved sectional area by photographing with a rotary arm turning while locally radiating conical X-ray beams constantly passing through only a specific region from an X-ray generator, conforming a rotating center of the rotary arm and a center of the specific region in the curved sectional area along a dental arc, which is an object to be examined, or inside of a bow-shape of the curved sectional area, the rotary arm including the X-ray generator and the two-dimensional X-ray image sensor facing to each other; arithmetically processing thus obtained X-ray projection image information by a backprojection method and computing a three-dimensional distribution information of an X-ray absorption coefficient of the curved sectional area; and calculating the three-dimensional distribution information of an X-ray absorption coefficient on a projection line intersecting a normal line of a panoramic image layer at a specified angle for any regions of the panoramic image layer of the curved sectional area and obtaining a panoramic X-ray image of the curved sectional area seen from the projection line by expanding the calculated result on a two-dimensional plane.

According to the X-ray CT method the rotary arm of following complicate loci doesn't require to form an envelope curve La (as in FIG. 6) as in the prior art for producing panoramic X-ray images. In the present invention, radiographing is performed with the center of rotation fixed. at a specific region. Therefore, the construction of the rotary arm can be simplified.

In this method, a conical X-ray beam is always radiated on a specific region in the curved sectional area along a dental arc, which is an object to produce a panoramic X-ray image, or inside of a bow-shape of the curved sectional area. When a panoramic X-ray image of an entire jaw is radiographed, the specific region is required to be outside of the curved sectional region and inside of the bow-shape of the curved sectional area. When a panoramic X-ray image of one side such as a right side or a left side is radiographed, the specific region may be inside of the curved sectional area. In other words, according to this method, the curved sectional region to be radiographed to produce an image and the specific region where X-ray conical beams are always radiates locally are basically different.

While the projection data is small that can be obtained with the conical X-ray beam locally radiated on the curved sectional region to produce a panoramic X-ray image, panoramic X-ray images clear enough for use in practice can be obtained. That is because the specific region selected is an area in the curved sectional region or in the bow-shape of the curved sectional region where there are less obstacles and, in addition, only a required X-ray projection image is appropriately extracted from the X-ray projection image produced by the conical X-ray beams.

As an example of the specific region, the region which includes excursion of an ortho-conical X-ray beam necessary for producing an ortho-radial panoramic X-ray image of the curved sectional area, is suitable. However, it may be a region in the curved sectional area and in the bow-shape of the curved sectional area. The specific region may be determined considering the projecting condition such as an ortho-radial panoramic radiography by an orth-conical X-ray beam and a normal panoramic radiography and the exposure dose. It is understood that the ortho-conical X-ray beam is a shape of a conical X-ray beam that is locally radiated to produce panoramic X-ray images roughly perpendicular to the curved sectional area, an ortho-radial panoramic X-ray image and it means a conical X-ray beam roughly perpendicular to the panoramic image layer in the curved sectional area extracted from the locally radiating conical X-ray beam. The reason why that ortho-conical X-ray beam alone is extracted is this. The partial X-ray projection images by the ortho-conical X-ray beam contain projection data most suitable for formation of panoramic X-ray images of the curved sectional region, that is, projection data in which teeth are less overlapped.

After selecting such a specific region, only partial X-ray projection images produced by the ortho-conical X-ray beam roughly perpendicular to the curved sectional area is taken out from the X-ray projection images of the curved sectional area sequentially produced on the two-dimensiona X-ray image sensor. The taken out partial X-ray projection images are arithmetically processed to obtain the three-dimensional distribution information of an X-ray absorption coefficient of the dental arc. Thereby, clear ortho-radial panoramic X-ray images can be obtained.

Furthermore, in this method, because a panoramic X-ray image which is an overlapping image seen from a projection line intersecting at a specified angle to a panoramic image layer for producing the panoramic X-ray image is obtained, foreign objects hidden if seen from one direction can be easily found, and because diverse sectional images changing a direction of the projection line for a same sectional image layer is obtained, how a tooth is overlapped with another can be more accurately diagnosed.

In case of producing panoramic X-ray images, panoramic sectional images seen from different directions of a projection line for the same sectional image layer can be provided as mentioned above so that the method of the present invention is highly useful for diagnosis (2) An X-ray computed tomography method is comprised of: sequentially obtaining on a two-dimensional X-ray image sensor an X-ray projection image information of a curved sectional area by photographing with a rotary arm turning while locally radiating conical X-ray beams constantly passing through only a specific region from an X-ray generator, conforming a rotating center of the rotary arm and a center of the specific region in the curved sectional area along a dental arc, which is an object to be examined, or inside of a bow-shape of the curved sectional area, the rotary arm including the X-ray generator and the two-dimensional X-ray image sensor facing to each other; arithmetically processing thus obtained X-ray projection image information by a backprojection method and computing a three dimensional distribution information of an X-ray absorption coefficient of the curved sectional area; and calculating the three-dimensional distribution information of an X-ray absorption coefficient on a projection line for any regions of the panoramic image layer of the curved sectional area, presetting a normal line of the panoramic image layer as the projection line, and obtaining a panoramic X-ray image of the curved sectional area seen from the projection line by expanding the calculated result on a two-dimensional plane.

This X-ray CT method defines the specified angle of the projection line and the normal line of the panoramic image layer in the X-ray CT method mentioned in (1) is set at 0 (zero) degree. Namely, the projection line conforms with the normal line.

In the prior panoramic X-ray imaging apparatus without using CT, an X-ray transmitted image including not only a three-dimensional distribution information of an X-ray absorption coefficient of a desired region for producing X-ray transmitted images but also information of an unnecessary region for producing images, therefore, the obtained images may be out of focus. Furthermore, X-ray incidence for a dental arch from a complete normal direction can't be achieved. Therefore, the obtained images aren't a complete ortho-radial panoramic X-ray image. However in this CT method, the three-dimensional distribution information of an X-ray absorption coefficient for the once obtained curved sectional area by local radiation is reconstructed so that only acceptable data among the obtained data, namely the data on a projection line while presetting a direction of a normal line for the panoramic image layer as a direction of the projection line, are used for producing a panoramic X-ray image, thereby an accurate ortho-radial panoramic X-ray image being obtained.

(3) According to this X-ray computed tomography method, in the X-ray computed tomography method in (1) or (2), a calculated result of a weighted average of the three-dimensional distribution information of an X-ray absorption coefficient on the projection line is expanded on a two-dimensional plane so as to obtain a panoramic X-ray image from the three-dimensional distribution information of an X-ray absorption coefficient of the curved sectional area.

According to this X-ray CT method, an operational method which isn't specified in (1) and (2) is defined to be a weighted average. According to the weighted average, experimentally obtained weighting can be done for each data in case of calculating from the three-dimensional distribution information so that more accurate panoramic X-ray image can be obtained. If any weighing isn't set for the weighted average, calculation is an arithmetic average.

(4) According to this X-ray computed tomography method, in the X-ray CT methods in (1) to (3), a direction of the projection line further becomes a direction of a normal line for a rising direction of each tooth constituting the dental arch corresponding to the curved sectional area.

The specified angle in (1) to (3) isn't always two-dimensional but may include a three-dimensional one. In this method, the specified angle is defied as an angle in which the direction of the projection line is the direction of the normal line for the rising direction of tooth.

In the prior panoramic X-ray image, because front teeth are inclined for a sectional image layer, images in which adjacent teeth are overlapped are obtained or images of accurate size can't be obtained. However, according to this method, images in which teeth are rarely overlapped can be obtained and accurate diagnosis of caries of adjacent teeth can be done, because images seen from the normal line of the rising direction of the teeth. Furthermore, caries diagnosis can be made at full scale.

(5) According to this X-ray computed tomography method, in the X-ray CT method in (1), the specified angle is constructed to be adjustable at an optional angle in up and down direction and/or right and left direction for the panoramic image layer. This method clears that the specified angle isn't limited to be two-dimensional and may be a three-dimensional angle including an up and down direction and/or a right and left direction for the panoramic image layer, like the method in (4). The method can correspond to the case where the rising direction and the overlapping direction of teeth are three-dimensionally inclined such as in up and down direction and/or in right and left direction.

(6) According to the X-ray computed tomography method, the specified angle of the X-ray CT methods in (1) to (5) is constructed so as to be equal for any regions of the panoramic image layer. In the present invention, the specified angle of the projection line and the normal line of the panoramic image layer may be basically different depending on each region. In this method, the specified angle is set equal for the panoramic image layer.

In such a manner, panoramic X-ray images seen from a direction of the projection line inclining at an equal angle for any regions of the panoramic image layer so that the images can be sensuously understood. (7) According to this X-ray computed tomography method, either the specified angle described in the methods (1), (5) or (6) is infinitely and variably adjustable or it is selectable from plural specified angles.

In this method, a setting method of the specified angle for determining a direction of the projection line is defined. (8) According to the X-ray computed tomography method, in the X-ray CT methods in (1) to (7), the object to be examined is moved for the rotating center of the rotary arm or the rotating center of the rotary arm is moved for the object to be examined for positioning so as to conform the rotating center of the rotary arm and the center of the specific region. According to this method, a method for conforming the rotating center of the rotary arm and the center of the specified region can be selected from two ways according to the target to be moved so that there are plural choices for conforming those centers.

(9) According to the X-ray computed tomography method, in the X-ray CT methods in (1) to (8), only ortho-conical X-ray beams which is approximately perpendicular to the panoramic image layer are extracted from the conical X-ray beams and are radiated, a partial X-ray projection image information obtained on the two-dimensional X-ray image sensor by the ortho-conical X-ray beams is arithmetically processed by a backprojection method and the three-dimensional distribution information of an X-ray absorption coefficient of the curved sectional area is obtained, and a panoramic X-ray image is obtained by expanding the three-dimensional distribution information on a two-dimensional plane.

According to this method, radiating beam is an ortho-conical X-ray beam from the first instead of extracting a partial X-ray projection image information presumably obtained by ortho-conical X-ray beams from the X-ray projection image information after radiating conical X-ray beams. Therefore, the ortho-conical X-ray beams are included in the conical X-ray beams so that exposed dose to the object to be examined can be more reduced.

(10) According to the X-ray computed tomography method, in the methods described in (1) to (9), X-rays are radiated on an object to be examined while the rotary arm is turned with an axial direction of the rotating axis of the rotary arm inclining at a specified angle for a perpendicular direction of the object or the rotary arm is turned with the object inclining at a specified angle for the axial direction of the rotating arm of the rotary arm.

According to this method, conical X-ray beams are radiated on the object while the rotary arm is turned with the axial direction of the rotating axis of the rotary arm inclining at a specified angle for the perpendicular direction of the object or the rotary arm is turned with the object inclining at a specified angle for the axial direction of the rotating arm of the rotary arm. Therefore, conical X-ray beams can be radiated in a direction so as not to transmit a cervix which becomes an affecting shadow and the affect of the affecting shadow can be reduced. In the latter method, the apparatus can be simplified because the direction of the object is inclined.

(11) According to the X-ray computed tomography method, in the methods of (1) to (9) X-rays are radiated on the object to be examined while the rotary arm is turned while making the rotating axis a given precession movement.

According to this method, X-rays are radiated on the object while the rotary arm is turned while making the rotary axis of the rotary arm a given precession movement, namely grinding movement wherein the rotary axis is turned around the precession axis with the rotary axis inclining at a specified angle to the precession axis at a center of the specified region, so that conical X-ray beams can avoid the affecting shadow which can't be avoided if they are radiated horizontally.

(12) An X-ray computed tomography apparatus is comprised of: a rotary arm with an X-ray generator and a two-dimensional image sensor faced to each other; position adjusting means for conforming a rotating center of the rotary arm and a center of a specific region in a curved sectional area along a dental arc, which is an object to be examined, or inside of a bow-shape of the curved sectional area; turning means for turning the rotary arm while locally radiating conical X-ray beams constantly passing through only the specific region from the X-ray generator; image storage means for sequentially storing an X-ray projection image information of the curved sectional area obtained on the two-dimensional X-ray image sensor by the X-ray conical beams; arithmetic processing means for calculating thus obtained X-ray projection image information by a backprojection method and computing a three-dimensional distribution information of an X-ray absorption coefficient of the curved sectional area; and angle setting means for setting a specified angle of a normal line of a panoramic image layer in the curved sectional area and a projection line intersecting the normal line; wherein the arithmetic processing means calculates the three-dimensional distribution information of the X-ray absorption coefficient on the projection line intersecting at the specified angle set by the angle setting means for any regions on the panoramic image layer, the calculated result is expanded on a two-dimensional plane, and a panoramic X-ray image of the curved sectional area seen from a direction of the projection line is obtained. This apparatus is to achieve the CT method of (1) and has the same effect as that of (1).

(13) An X-ray computed tomography apparatus is comprised of: a rotary arm with an X-ray generator and a two-dimensional image sensor faced to each other; position adjusting means for conforming a rotating center of the rotary arm and a center of a specific region in a curved sectional area along a dental arc, which is an object to be examined, or inside of a bow-shape of the curved sectional area, turning means for turning the rotary arm while locally radiating conical X-ray beams constantly passing through only the specific region from the X-ray generator; image storage means for sequentially storing an X-ray projection image information of the curved sectional area obtained on the two-dimensional X-ray image sensor by the conical X-ray beams; arithmetic processing means for calculating thus obtained X-ray projection image information by a backprojection method and computing a three-dimensional distribution information of an X-ray absorption coefficient of the curved sectional area; and angle setting means for setting a specified angle of a normal line of a panoramic image layer in the curved sectional area and a projection line intersecting the normal line; wherein the angle setting means sets the specified angle in such a manner that a direction of the projection line conforms to a direction of the normal line of the panoramic image layer for any regions on the panoramic image layer of the curved sectional area, the arithmetic processing means calculates the three-dimensional distribution information of the X-ray absorption coefficient on the projection line for the regions, the calculated result is expanded on a two-dimensional plane, and a panoramic X-ray image of the curved sectional area seen from a direction of the projection line is obtained.

This apparatus is to achieve the CT method of (2) and has the same effect as that of (2).

(14) According to the X-ray computed tomography apparatus, in the X-ray CT apparatus of (12) or (13), the arithmetic processing means expands a calculated result of a weighted average of the three-dimensional distribution information of the X-ray absorption coefficient on the projection line on the two-dimensional plane so as to obtain a panoramic X-ray image from the three-dimensional distribution information of the X-ray absorption coefficient of the curved sectional area.

This apparatus is to achieve the CT method of (3) and has the same effect as that of (3).

(15) According to the X-ray computed tomography apparatus, in the X-ray CT apparatus of (12) to (14), the angle setting means is further constructed in such a manner that a direction of the projection line also becomes a direction of a normal line for a rising direction of each tooth constituting the dental arch corresponding to the curved sectional area.

This apparatus is to achieve the CT method of (4) and has the same effect as that of (4).

(16) According to the X-ray computed tomography apparatus, in the X-ray CT apparatus of (12), the angle setting means is constructed in such a manner that the specified angle is adjustable at an optional angle in up and down direction and/or in right and left direction for the panoramic image layer. This apparatus is to achieve the CT method of (5) and has the same effect as that of (5).

(17) According to the X-ray computed tomography apparatus, in the X-ray CT apparatus of (12) or (16), the angle setting means is constructed in such a manner that the specified angle is equal for any regions of the curved sectional area. This apparatus is to achieve the CT method of (6) and has the same effect as that of (6).

(18) According to the X-ray computed tomography apparatus, in the X-ray CT apparatus of (12), (16) or (17), the angle setting means is comprised of variable means for infinitely and variably adjusting the specified angle and/or selection means for selecting the specified angle from predetermined plural angles. This apparatus is to achieve the CT method of (7) and has the same effect as that of (7).

(19) According to the X-ray computed tomography apparatus, in the X-ray CT apparatuses of (12) to (18), the position adjusting means is constructed in such a manner that the object to be examined is moved for the rotating center of the rotary arm or the rotating center of the rotary arm is moved for the object to be examined for positioning so as to conform the rotating center of the rotary arm and the center of the specific region.

This apparatus is to achieve the CT method of (8) and has the same effect as that of (8).

(20) According to the X-ray computed tomography apparatus, the X-ray CT apparatuses of (12) to (19) is further comprised of X-ray beam width restriction means for extracting and radiating only ortho-conical X-ray beams which are approximately perpendicular to the panoramic image layer from the conical X-ray beams, and wherein the arithmetic processing means arithmetically processes a partial X-ray projection image information obtained on the two-dimensional X-ray image sensor by the ortho-conical X-ray beams by a backprojection method and the three-dimensional distribution information of the X-ray absorption coefficient of the curved sectional area is obtained, and a panoramic X-ray image is obtained by expanding thus obtained three-dimensional distribution information on the two-dimensional plane.

(21) According to the X-ray computed tomography apparatus, in the X-ray CT apparatuses of (12) to (20), X-rays are radiated on the object to be examined while the rotary arm is turned with the axial direction of the rotating axis of the rotary arm inclining at a specified angle for a perpendicular direction of the object by providing rotating axis direction setting means capable of inclining the axial direction of the rotating axis of the rotary arm or X-rays are radiated on the object to be examined while the rotary arm is turned with the object inclining at a specified angle for the axial direction of the rotating center of the rotary arm by providing object supporting direction setting means capable of inclining the object's supporting direction.

This apparatus is to achieve the CT method of (10) and has the same effect as that of (10).

(22) According to the X-ray computed tomography apparatus, in the X-ray CT apparatuses of (12) to (20), the turning means is constructed in such a manner that the rotary arm is turned while making the rotating axis of the rotary arm a given precession movement.

This apparatus is to achieve the CT method of (11) and has the same effect as that of (11).

(23) According to the X-ray computed tomography apparatus, in the X-ray CT apparatuses of (12) to (22), the curved sectional area is any one of a local region where a few teeth are rising, a temporomandibular joint region or an otorhinolaryngologic region.

According to this apparatus, the curved sectional area is one of a local region where a few teeth are rising, a temporomandibular joint region or an otorhinolaryngologic region. In this case, panoramic X-ray images seen from optional projection lines can be obtained for these regions in a same manner.

(24) According to the X-ray computed tomography apparatus, the X-ray CT apparatuses of (12) to (23) are further comprised of display means capable of sequentially displaying the panoramic X-ray image obtained while setting the specified angle by means of the angle setting means.

This apparatus has display means capable of sequentially displaying the panoramic X-ray image obtained while changing the specified angle by means of the angle setting means. Therefore, the images in which a specified angle is seen from varied directions can be obtained according to diagnosis purposes so that such an apparatus has a high diagnosis value.

(25) According to the X-ray computed tomography apparatus, the display means of the X-ray CT apparatus in (24) can sequentially show the panoramic X-ray image obtained while continuously changing the specified angle by means of the variable means of the angle setting means described in (18).

According to this apparatus, the display means of (24) is defined to display panoramic X-ray images while continuously changing the direction of the projection line so that it has a high diagnosis value.

(26) According to the X-ray computed tomography apparatus, in the X-ray CT apparatus of (24), the display means can combine a panoramic X-ray image of an upper jaw and a panoramic X-ray image of a lower jaw, both obtained by the apparatus of (15), into one panoramic X-ray image for displaying, the panoramic X-ray image of the upper jaw being obtained by setting a normal line direction for a rising direction of a tooth of a curved sectional area along the upper jaw as a projection line and the panoramic X-ray image of the lower jaw being obtained by setting a normal line direction for a rising direction of a tooth of a curved sectional area along the lower jaw.

According to this apparatus, the CT method of (15) is separately used for the curved sectional area of the upper jaw and that of the lower jaw and the display means of (24) is defined to display one combined panoramic X-ray image of thus obtained panoramic X-ray image of the upper jaw and thus obtained panoramic X-ray image of the lower jaw. Therefore, images corresponding to each rising direction of teeth can be obtained so that such images have high a diagnosis value.

(27) According to the X-ray computed tomography apparatus, in the apparatuses of (24) to (26), the display means can select plural panoramic X-ray images obtained under different conditions and display in array on the same screen. According to this apparatus, as plural panoramic X-ray images can be selected and displayed in array on the same screen, displaying images can be selected according to diagnosis purposes, thereby achieving convenience.

(28) According to the X-ray computed tomography apparatus, in the apparatus of (27), the display means can display the panoramic X-ray image obtained in (12) and the panoramic X-ray image obtained in (13) in array on the same screen, the panoramic X-ray image obtained in (12) being seen from the projection line intersecting the normal line of the panoramic image layer at a specified angle and the panoramic X-ray image obtained in (13) being seen from the projection line by setting the normal line of the panoramic image layer as the projection line. According to this apparatus, the display means of (27) is defined to display in array the panoramic X-ray images seen from an optional direction of the projection line and the panoramic X-ray images seen from the normal line, like the prior art. Such an apparatus is useful for comparing and judging the images.

(29) According to the X-ray computed tomography apparatus, at least one of functions same as operated in the apparatuses of (12) to (28) can be selectively operated. Therefore, several types of panoramic X-ray images can be obtained and shown by one apparatus so that it is useful for diagnosis.

BRIEF DESCRIPTION OF THE DRAWINGS

FIG. 18 is a conceptual diagram for explaining still another production method of panoramic X-ray images of the present invention.

FIG. 20 is an example wherein the X-ray panoramic X-ray image production method of FIG. 19 is applied for other teeth.

FIG. 26 illustrates conditional functions used in an X-ray CT method of the present invention.

FIG. 31 shows arithmetical expressions (formula 1) to (formula 4) used for analyzing the basic principle of an X-ray CT.

FIG. 32 shows arithmetical expressions (formula 5) to (formula 8) used for analyzing the principle of an X-ray CT of this invention.

FIG. 33 shows arithmetical expressions (formula 9) to (formula 12) used for analyzing the basic principle of an X-ray CT for producing a panoramic X-ray image.

DESCRIPTION OF THE INVENTION

The present invention will be described referring to the attached drawings herein after wherein the embodiment is described as a representatively used X-ray computed tomography, however, the present invention should not be limited to such an X-ray computed tomography.

Figure 1A:
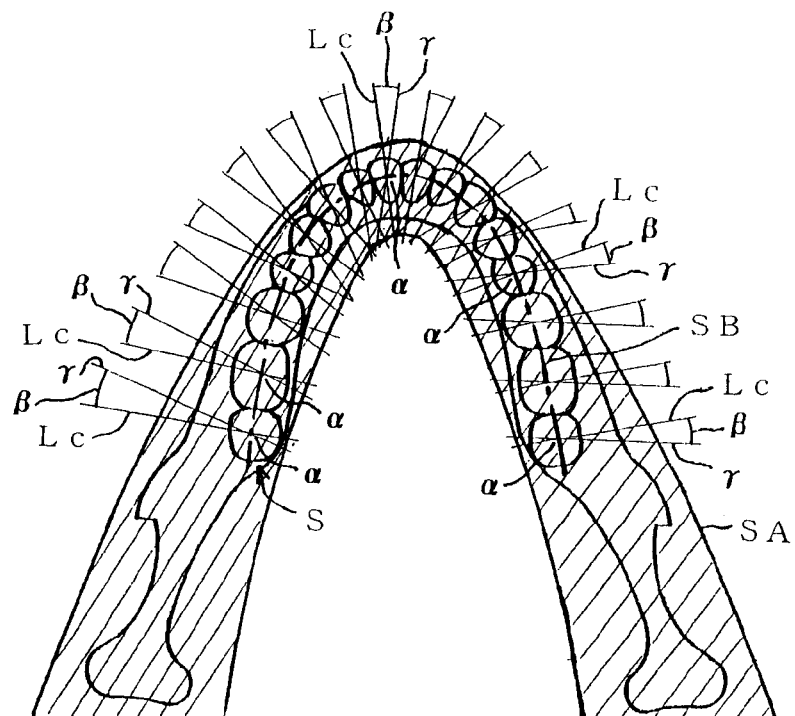
FIG. 1a and FIG. 1b illustrate a basic principle of producing panoramic X-ray images of a dental arch by means of an X-ray computed tomography (CT) method of the present invention.
Figure 1B:
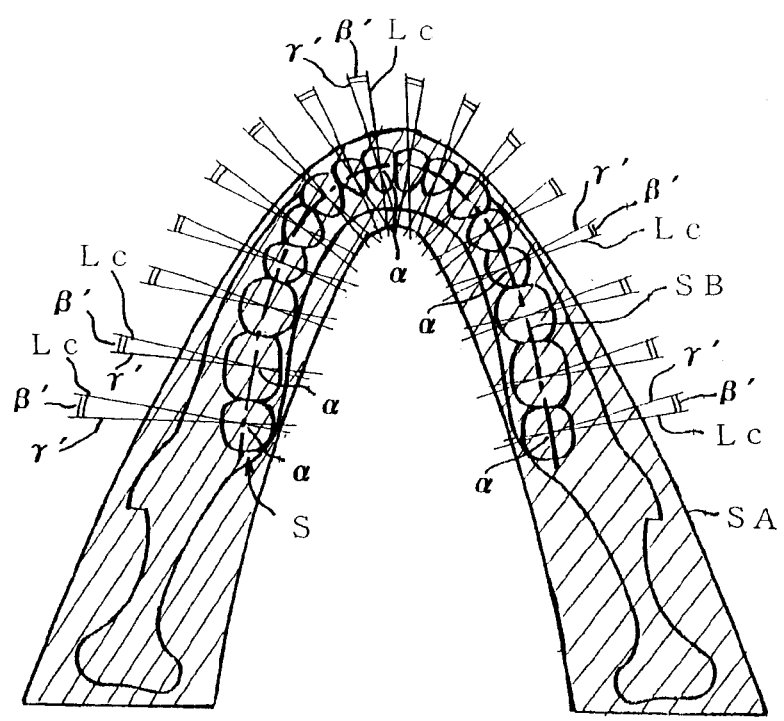

FIG. 1a and FIG. 1b show a basic principle of producing a panoramic X-ray image of a dental arch by means of an X-ray computed tomography (CT) method of the present invention.

Figure 24A:
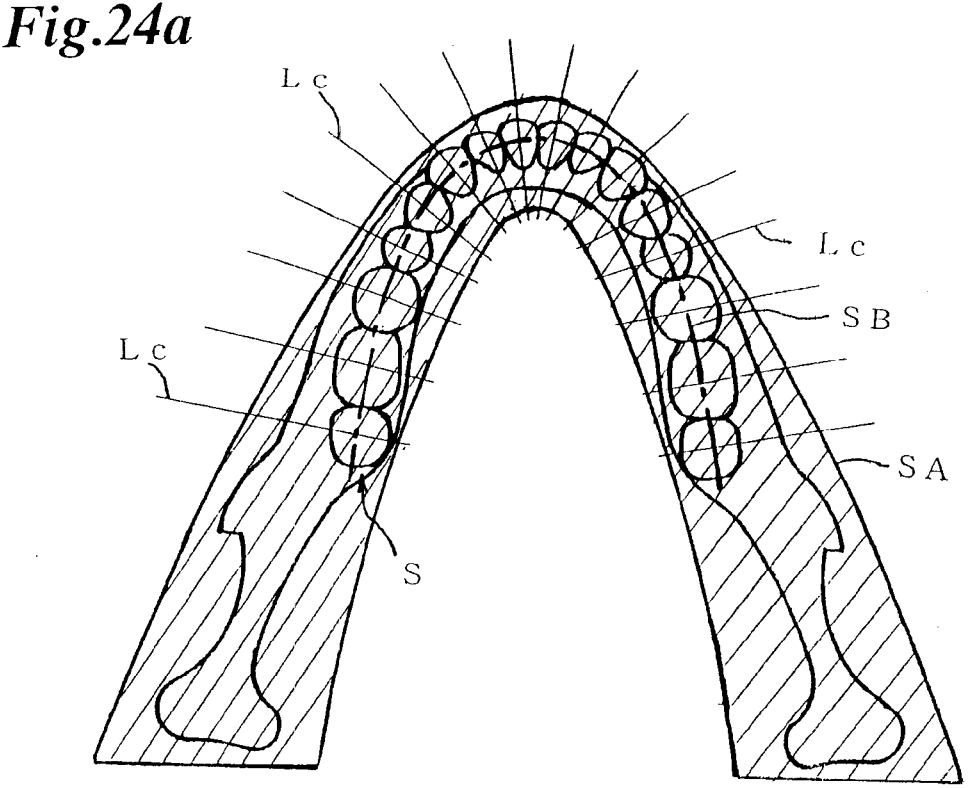
FIG. 24a is a plane view conceptually showing the area of the three-dimensional distribution information of an X-ray absorption coefficient obtained by the X-ray CT apparatus.
Figure 24B:
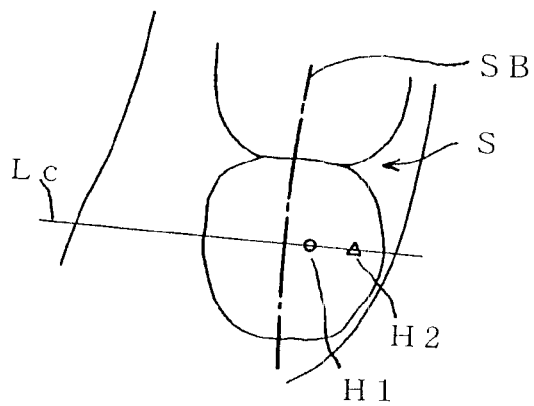
FIG. 24b is a partial plane view for conceptually showing the conventional method for producing panoramic X-ray images from the distribution information and FIG. 24c is a partial view of a panoramic X-ray image produced by this method.

In this figure, S is a dental arch, SA is the curved sectional area where a three-dimensional distribution information of an X-ray absorption coefficient is obtained, SB is a panoramic image layer of the curved sectional area SA, Lc is a normal line to the panoramic image layer SB, same as the prior art in FIG. 24.

On the other hand, this invention is characterized in the following: In order to produce panoramic X-ray images based on the three-dimensional distribution information of an X-ray absorption coefficient, regarding each element α on the panoramic image layer SB of the dental arch S, the information on a normal line Lc is not used but the arithmetical average of the three-dimensional distribution information of an X-ray absorption coefficient on a projection line γ oblique at a specified angle β to the normal line Lc is used. In this case the specified angle β is the same with respect to any elements a of the dental arch S.

By this method, a panoramic X-ray image seen from the projection lineγ oblique by a specified angle β to the normal line Lc to the panoramic image layer SB comprising the sectional image of the dental arch S is available. Diagnosis of proximal surfaces of adjacent teeth can be easily done. It is also possible to distinguish foreign objects, the overlap of teeth and the area of dental caries, which would be impossible from a panoramic X-ray image seen from one direction.

This determined angle could be an angle β' which is oblique on the other side of β to the normal line Lc as shown in FIG. 1b. This enables production of a panoramic X-ray image seen from the projection line γ' oblique with an angle β to the normal line Lc, which makes foreign objects or caries to be found more easily.

Also, the specified angle could be changed continually from one direction to others to the normal line Lc as a panoramic image layer. This makes it possible to continually see the panoramic X-ray images oblique with a specified angle, which is convenient for dental practice, etc.

The specified angle β or β' could be different for each element α. They could also be diversified three-dimensionally, not limited to two-dimensionally. For example, the normal line could be in the rising direction of each tooth or they could be different depending on teeth, for which examples will be explained later.

FIG. 1a and FIG. 1b show an embodiment for producing a panoramic X-ray image, however, such a method for obtaining different panoramic X-ray images by changing the panoramic image layer and the direction of a projection line to the panoramic image layer can be applicable to obtain several kinds of sectional images by designating the sectional image layer and the projection line to the sectional image layer for the local region from which a three-dimensional distribution information of an X-ray absorption coefficient is obtained.

Figure 2A:
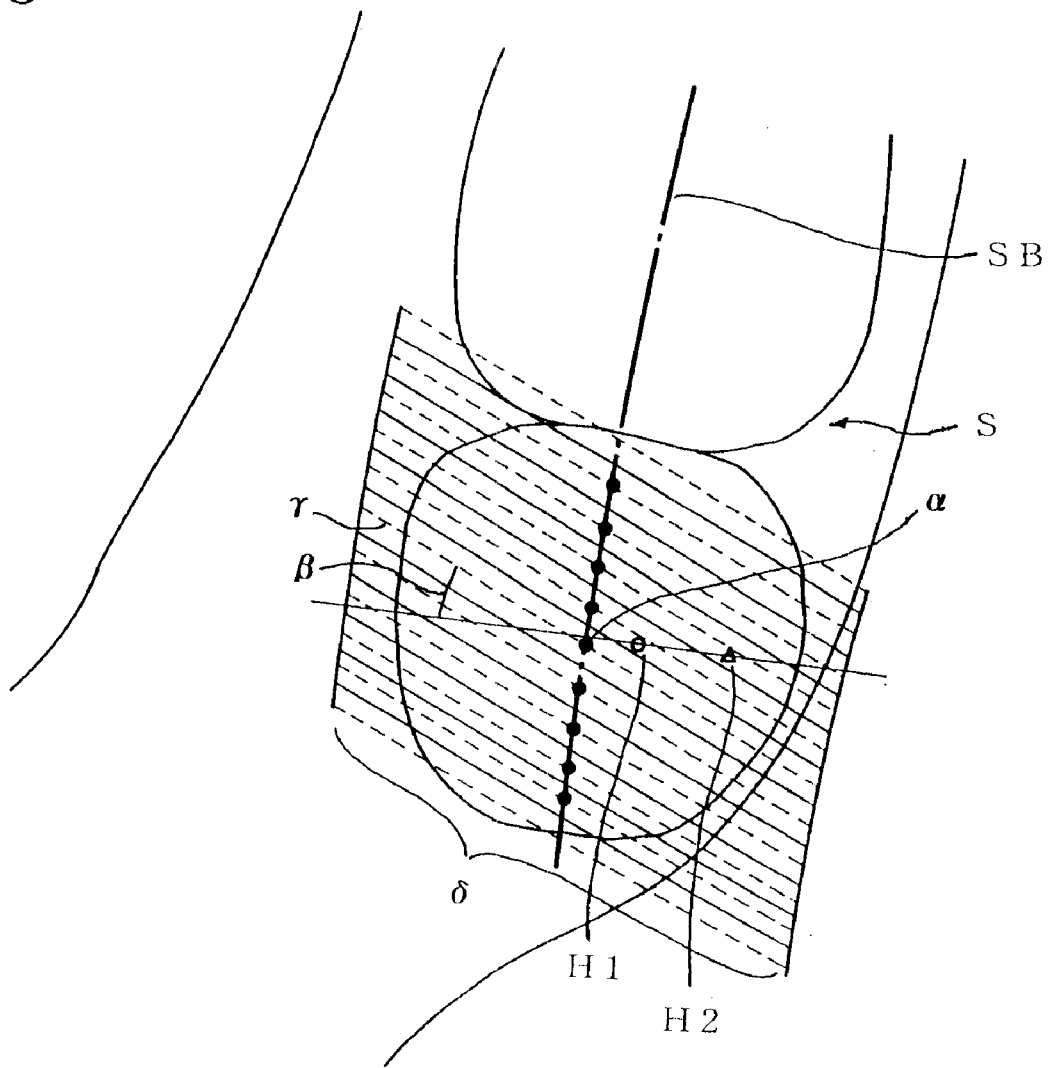
FIG. 2a is an enlarged view of a part of FIG. 1a and focuses on a cheek tooth at the left-hand side.
Figure 2B:
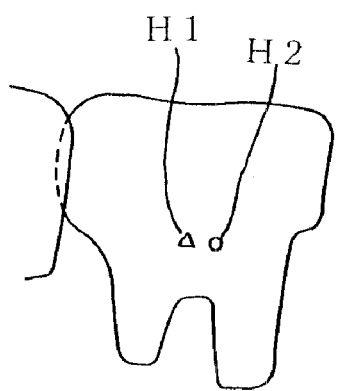
FIG. 2b is a part of a panoramic X-ray image produced by this method.

FIG. 2a is an enlarged view of a part of FIG. 1a and focuses on a cheek tooth at the left hand side, and FIG. 2b is a part of a panoramic X-ray image produced by this method. The members already explained regarding FIG. 1 are referenced as the same reference numbers and characters and their explanations are omitted hereinafter.

H1 and H2 are foreign objects existing in the cheek tooth at left as in the case of FIG. 24. δ shows the area extracting the three-dimensional distribution information of an X-ray absorption coefficient to compute the arithmetical average for the element α as a center.

Figure 24C:
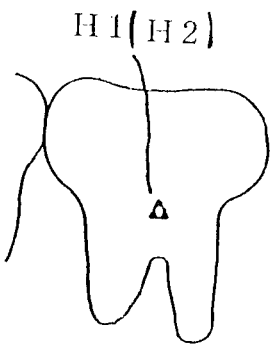

In the embodiment shown in FIG. 2a, foreign objects H1 and H2 influence the arithmetical average of different elements α. In the panoramic X-ray images made with this method, foreign objects H1 and H2 appear separately, which is shown in FIG. 2b. The difference compared to the result from the example in FIG. 24c is obvious.

In this method, the specified angle β could be set as desired. For example, in case of producing conventional panoramic X-ray images, it should be set to 0. In addition it is not necessary to radiate an X-ray for changing the angle because this method only recalculates the once obtained three-dimensional distribution information of an X-ray absorption coefficient. It is an advantage of an X-ray computer tomography-, which this method utilizes. The examiner could produce panoramic X-ray images from various directions of the object with limited number of X-ray radiation. As a result, the examiner could get more important information and at the same time reduce the burden to the patient.

This embodiment refers to a case producing panoramic X-ray images of the dental arch but this principle can be applied to the case the target local region is not a curved sectional area such as a dental arch but the local region where one or several teeth is rising, a temporomandibular joint area, and an otorhinolaryngological area. This method is effective for this case as well. This method also applies to the tomography from any direction of the area.

By adjusting the extracting area δ, the area appearing in the panoramic X-ray image can be adjusted and the affecting shadow can be removed.

Now the X-ray CT method and the apparatus of the present invention will be explained in detail and comprehensively.

Figure 3:
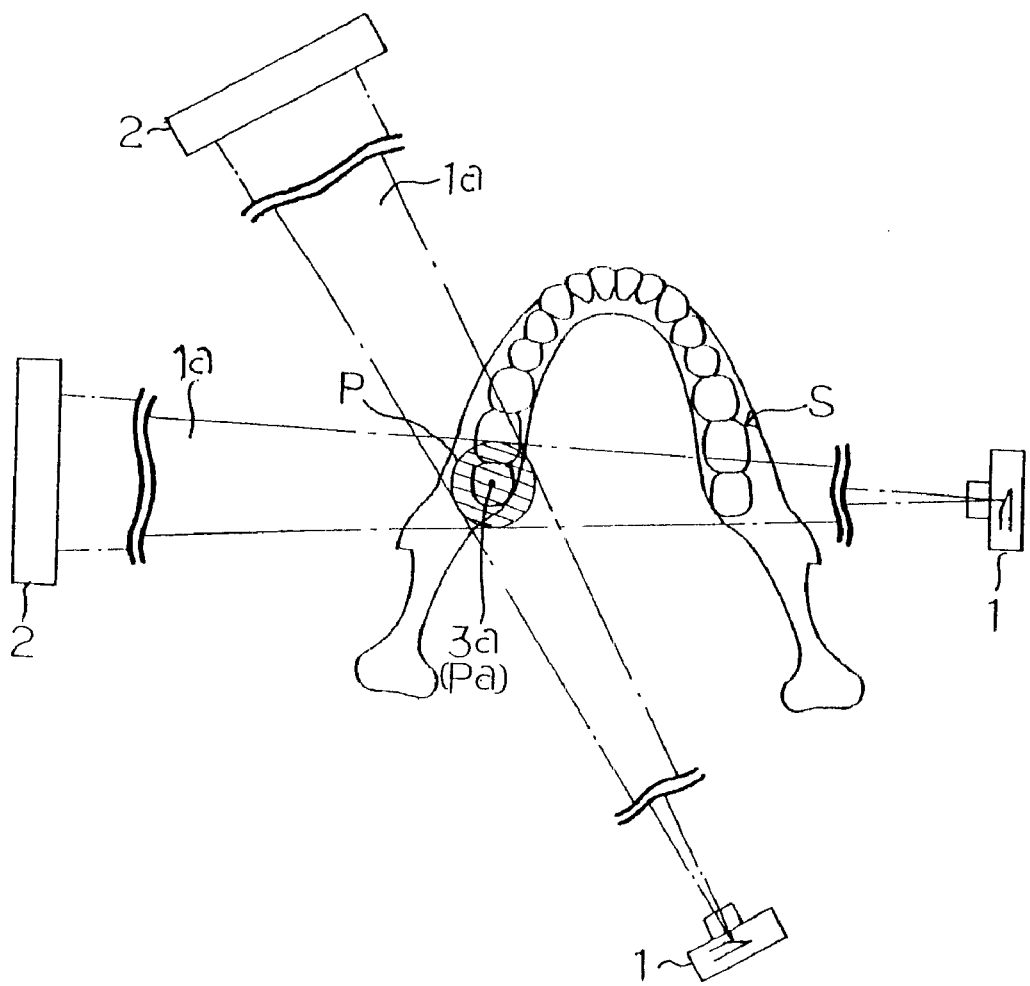
FIG. 3 illustrates a basic principle of an X-ray CT method of the present invention (when cheek teeth are projected).
Figure 4:
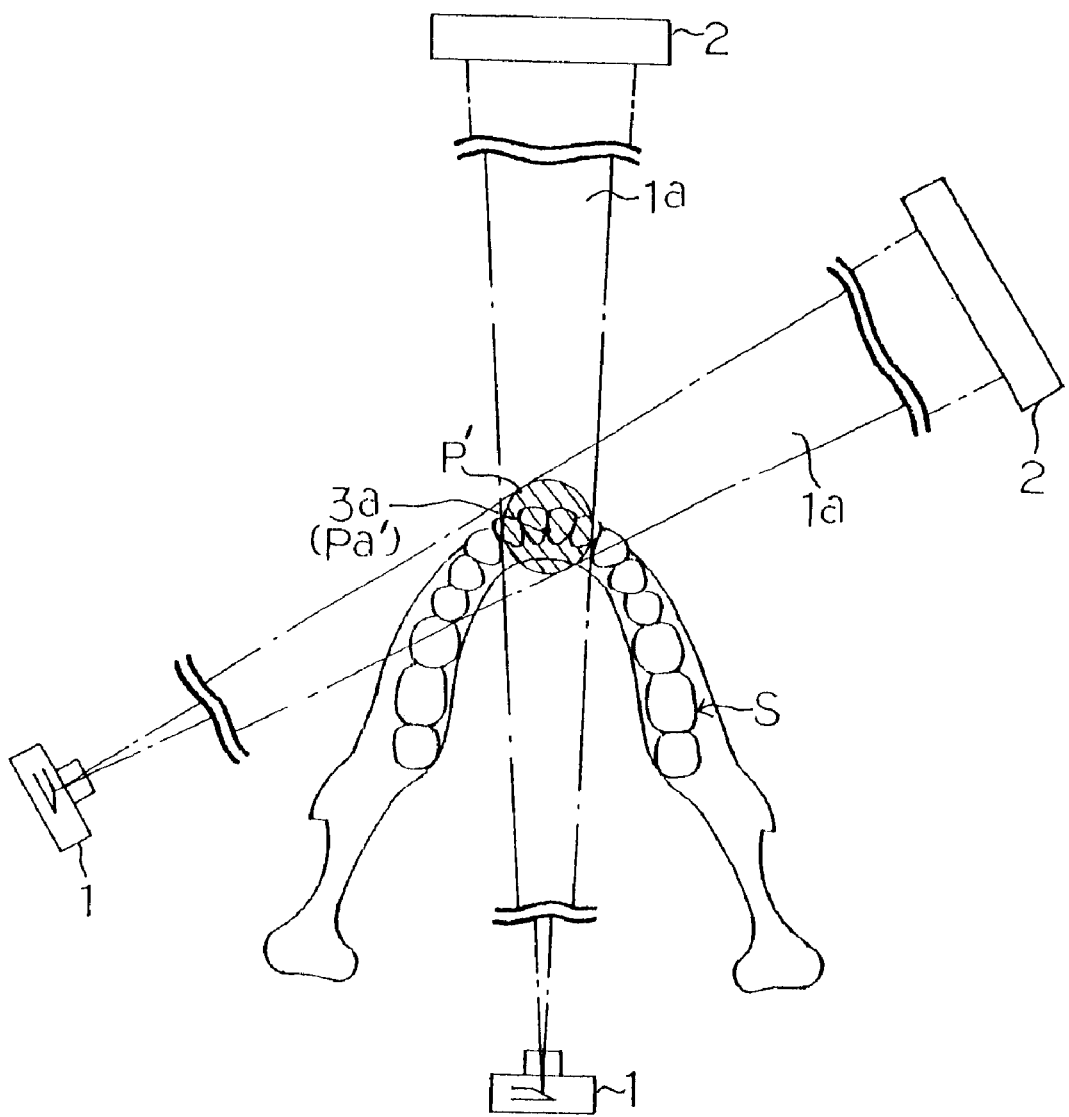
FIG. 4 illustrates a basic principle of another X-ray CT method of the present invention (when front teeth are projected).

FIG. 3 and FIG. 4 show a basic principle of an X-ray computed tomography (CT) method of the present invention. An embodiment wherein this CT method is applied for a local region is explained hereunder.

In these figures, the reference numeral 1 shows an X-ray generator and 2 shows a two-dimensional X-ray image sensor. They are faced to each other and provided for a rotary arm 3 which will be explained referring to FIG. 10 hereinafter. The reference characters P and P' show cheek teeth and front teeth, which are local regions to be projected respectively and S shows a dental arch.

According to the projection method of the present invention, as shown in FIG. 3 and FIG. 4, the rotary arm 3 is rotated at a constant velocity around center positions Pa, Pa' of the local regions P, P' on a center 3a thereof. In this case, the X-ray generator 1 emits a conical X-ray beam 1a having a beam width to include only the local regions P, P'. Therefore, an X-ray projection image of the local regions P, P' having a fixed pace of expansion is sequentially generated at a projection surface 2a of the two-dimensional X-ray image sensor 2.

As a two-dimensional X-ray image sensor, an X-ray TFT (Thin Film Transistor) sensor, an X-ray MOS (Metal Oxide Semiconductor) sensor, an X-ray II (Image Intensifier) camera, an X-ray amorphous serene sensor, an X-ray CCD (Charge Coupled Device) sensor, and an X-ray CCD sensor (XICCD) with an amplifier are used.

Thus projected X-ray projection image is processed with a backprojection and so on by a computer and a three-dimensional distribution information of an X-ray absorption coefficient in the local regions P, P' can be taken out as an image information. Therefore, when an optional section of the local regions P, P' is specified or predetermined, the sectional image can be obtained.

Here the sectional image layer corresponds to a panoramic image layer in case of obtaining a panoramic X-ray image. It is a projection image projecting the three-dimensional distribution information on a normal line to the designated sectional image layer and isn't an image taken out only the three-dimensional distribution information on the sectional image layer.

The rotary arm 3 is rotated conforming the center 3a of the rotary arm 3 and the centers Pa, Pa' of the local regions P, P'. In this case, the conical X-ray beam 1a is locally radiated so as to always include only the local regions P, P'. According to the projection condition, if at least the local regions P, P' are radiated half cycle, an optional sectional image of the region can be produced.

Figure 5A:
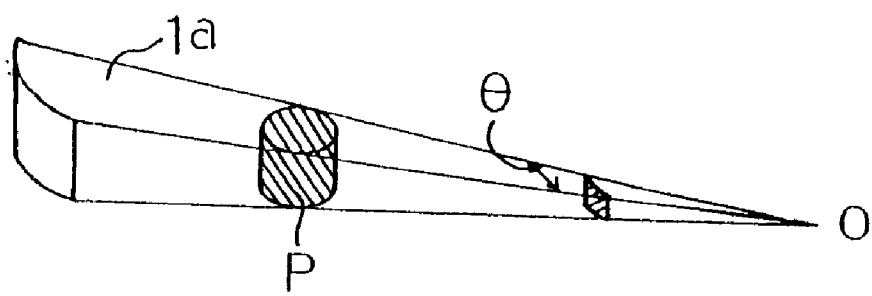
FIG. 5a and FIG. 5b are explanatory views comparing a conical X-ray beam and a fan shaped X-ray beam.
Figure 5B:
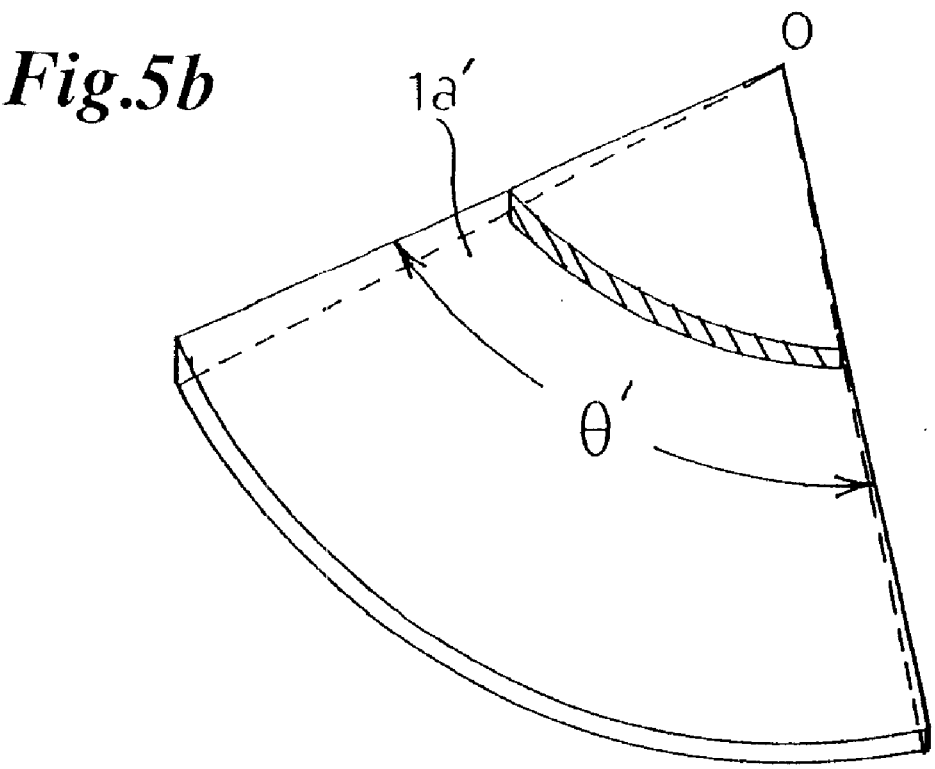

FIG. 5a is a detailed view of the conical X-ray beam radiated from the X-ray generator 1 and FIG. 5b is a conventional fan shaped X-ray beam 1a'.

The conical X-ray beam 1a has a small angle θ enlarging in a scanning direction and has a fixed thickness vertically comparing to that the conventional fan shaped X-ray beam 1a has a large angle θ' enlarging in a scanning direction and has small vertical spreading. The conical X-ray beam 1a is a beam bundle, which can cover the whole local region P to be projected at one beam radiation.

The conical X-ray beam 1a can be formed at an optional sectional shape. When the sectional shape is rectangular and the conical X-ray beam 1a is radiated from all the circumference at only one part of an object to be projected (called an object hereinafter), the local region P to which the conical X-ray beam 1a is commonly and locally radiated becomes cylindrical as shown in FIG. 5a. Therefore, the inside three-dimensional distribution information of an X-ray absorption coefficient can be calculated and the sectional image of an optional section inside the cylinder area can be obtained. When the section is made circular and the conical X-ray beam 1a is locally radiated only at a part of the object, the part where the conical X-ray beam 1a is commonly radiated becomes spherical. Therefore, the inside three-dimensional distribution information of an X-ray absorption coefficient can be calculated and the sectional image of an optional section in the sphere can be obtained.

When the X-ray CT method is used for dental care, a two-dimensional X-ray image sensor with 10 cm height and 10 cm width is used. In such a case, the cylinder, namely a local region, becomes 5 cm diameter and 5 cm height.

The rotary angle of the rotary arm 3 can be set accordingly from 5° to 360°. For example, it is divided into two by a direction perpendicular to a target sectional plane. When the arm 3 is rotated at least 5° equally divided by the direction vertical to the section to be projected, the sectional image can be produced from the X-ray projection data. On the other hand, the arm 3 should be rotated more than 180° and conventionally often 360° in order to produce all the optional sectional image of the local region P. If it is rotated 360°, the resolution can be made all around. However, it may be rotated from 180° to 360°.

Then the X-ray CT method for producing a panoramic X-ray image of a curved sectional area along a dental arch will be explained hereinafter.

Figure 6:
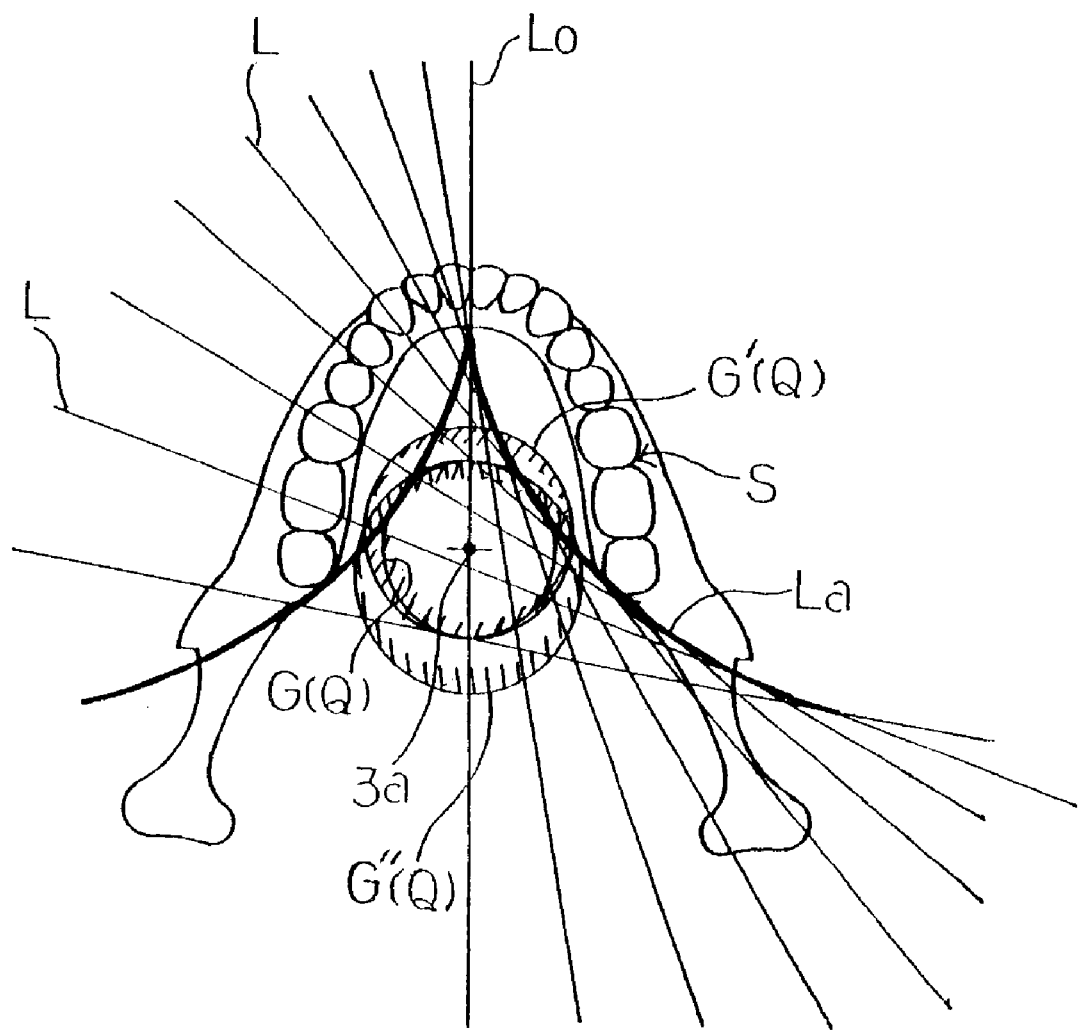
FIG. 6 illustrates a specific region of a center of a rotary arm for executing an X-ray CT method for producing a panoramic X-ray image.

FIG. 6 explains a local region for setting a position of the center 3a of the rotary arm 3 which is used for executing an X-ray CT for producing a panoramic X-ray image.

In the X-ray CT method for producing a panoramic X-ray image of the dental arch S according to the present invention, the center 3a of the rotary arm 3 is aligned to the center of a specific region (or a specific region of the curved sectional area SA or a specific region inside of a bow-shape of the curved sectional area SA) on the axis of symmetry Lo at the center of the curved sectional area SA. And while the rotary arm 3 is rotated at a constant velocity within a rotary angle according to the projection condition, the conical X-ray beam 1a of a fixed width is locally radiated and the X-ray projection image of the curved sectional area SA is obtained.

Generally, when a normal film-type panorama projection is executed, it is required that an X-ray beam bundle is moved while moving the center of the rotary arm during projection in such a manner that X-ray beams are preferably perpendicular to all the tooth rising in the curved sectional area SA. Such an X-ray beam bundle is shown as L in FIG. 6.

When an orthogonal X-ray beam bundle L . . . for all the tooth of the curved sectional area SA is drawn, an envelope curve La of these X-ray beam bundles L . . . is formed. Then an encircle G which touches internally to the envelope curve La is considered, all the X-ray beam bundles L for the curved sectional area SA passes through the encircle G.

Therefore, according to the X-ray CT of the present invention, for example, a center Ga of the encircle G is conformed with the rotating center 3a of the rotary arm 3 and radiography is executed by turning the rotary arm without moving the center thereof. In this case the conical X-ray beam 1a having a fixed width is locally radiated from circumference so as to locally radiate the encircle G, the conical X-ray beam 1a always includes an X-ray beam orthogonal to the curved sectional area SA (hereinafter the beam is called as an ortho-conical X-ray beam).

Figure 7:
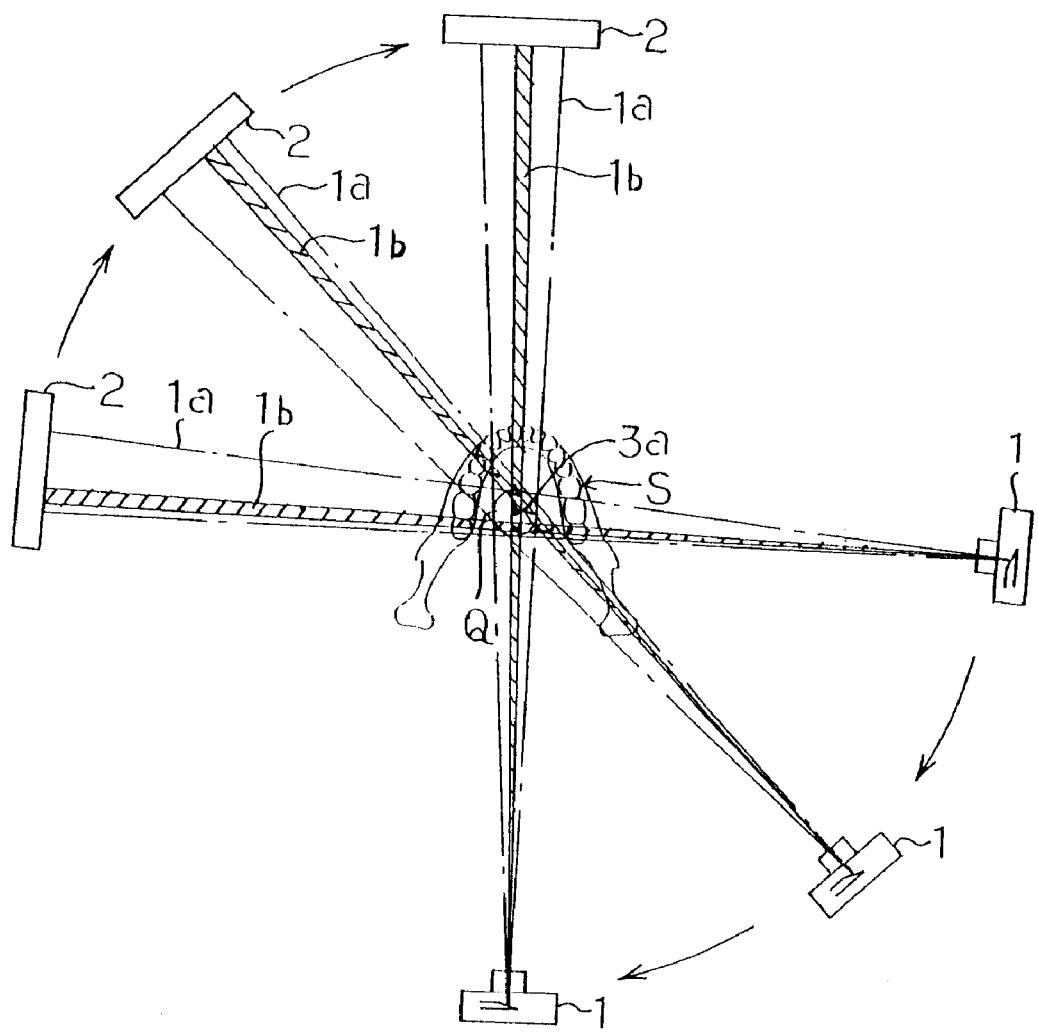
FIG. 7 shows an X-ray CT projection method for producing a panoramic X-ray image according to the present invention.

That is, in this example, the encircle G becomes the above-mentioned local region as shown in FIG. 7 and the region is represented by the reference character Q. The X-ray beam bundle orthogonal to each tooth is the above-mentioned ortho-conical X-ray beam and is represented by the reference number 1b.

When the conical X-ray beam 1a is locally radiated so as to form the specific region Q, the partial X-ray projection image formed by the ortho-conical X-ray beam 1b approximately orthogonal to the curved sectional area SA is extracted from the X-ray projection images of the curved sectional area SA sequentially produced on the two-dimensional X-ray image sensor 2. Then a three-dimensional distribution information of an X-ray absorption coefficient of the curved sectional area SA is taken out as an image information by processing the image and a continuous ortho-radial panoramic X-ray image of the curved sectional area SA can be produced.

The X-ray CT method of the present invention to produce a panoramic X-ray image of the curved sectional area SA is based on such a theory. The position of the center 3a of the rotary arm 3 and the width of the conical X-ray beam 1a, namely the position and dimension of the region Q, are properly set according to the mode of the image to be produced finally. In a word, the ortho-conical X-ray beam complying with the mode of the image is designed to be included in the conical X-ray beam.

For example, the position of the center 3a of the rotary arm 3 and the width of the conical X-ray beam which are set at projection, namely the specific region Q, aren't limited in the encircle G which touches internally to the above-mentioned envelope curve La. They may be a circle including the encircle G shown as G' or G" in FIG. 6. If such a circle is defined as the specific region Q, the center of the area is always positioned on the axis of symmetry Lo inside of the dental arch S. (In FIG.6 the center position of the rotary arm 3 is shown as 3a' and 3a" if the specific region Q is an encircle G' and G".)

A panoramic X-ray image isn't limited to an ortho-radial panoramic X-ray image and there are a standard panoramic X-ray image, a jawbone panoramic X-ray image, and a panoramic X-ray image on one side such as right or left. So, a conical X-ray beam isn't necessarily orthogonalized to the dental arch S. Therefore, when a panoramic X-ray image by such a projection method is produced, the position of the center 3a of the rotary arm 3 on the axis of symmetry Lo of the dental arch S and the width of a conical X-ray beam 1a, namely the specific region Q, are required to be determined so as to include these all ortho-conical X-ray beam 1b. One of the examples is the above-mentioned encircles G', G". In case of picturing a panoramic X-ray image of one side, the center 3a of the rotary arms may be in the curved sectional area SA or it may not be always on the axis of symmetry Lo.

The specific region Q for producing the panoramic X-ray image is decided corresponding to the panoramic X-ray image to be produced. In view of abatement of an X-ray exposed dose, it goes without saying that the area Q is preferably small.

As shown in FIG. 6, the rotary arm 3 isn't required to be rotated 360° and may be rotated 180° or more to 360° to picture an image. Therefore, an X-ray exposed dose and a projection time can be reduced at the rate of the reduced angle.

Figure 8:
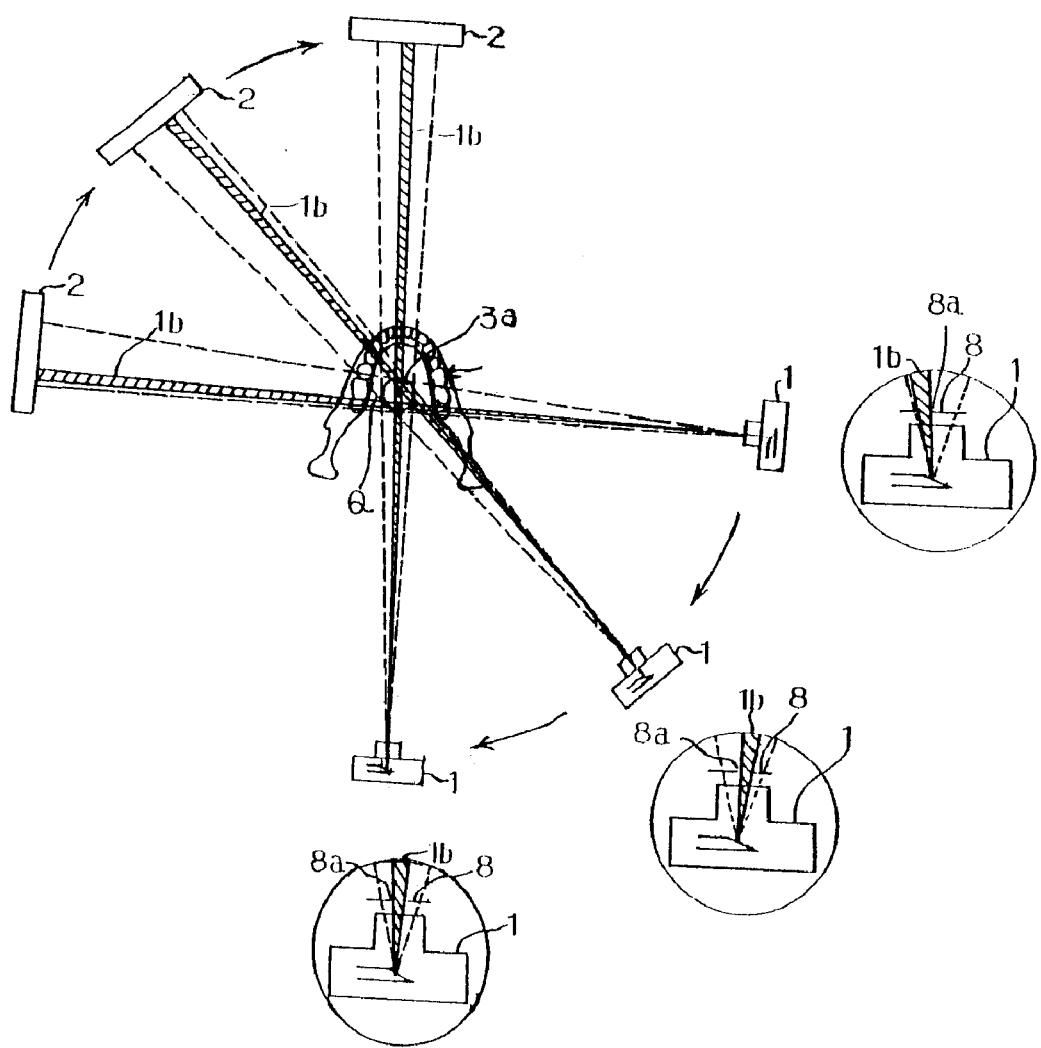
FIG. 8 shows an X-ray CT projection method for producing a panoramic X-ray image using a radiation control slit according to the present invention.

FIG. 7 and FIG. 8 show an X-ray CT method for producing a panoramic X-ray image of the present invention.

In FIG. 7 the center 3a of the rotary arm 3 and the width of the conical X-ray beam 1a are fixedly supported so as to form the specific region Q shown in the figure and the rotary arm 3 is rotated at a constant velocity. While the X-ray generator 1 radiates a conical X-ray beam 1a having a fixed width in a scanning direction according to rotation of the arm 3, an X-ray projection image of the curved sectional area SA is sequentially produced on the two-dimensional X-ray image sensor 2 by the conical X-ray beam 1a. Only a partial X-ray projection image produced by the ortho-conical X-ray beam 1b approximately orthogonal to the dental arch S is extracted among the radiation bundle of the conical X-ray beam 1a for thus produced X-ray projection image. The extracted partial X-ray projection image is processed and a three-dimensional distribution information of an X-ray absorption coefficient is taken out as an image information, thereby the panoramic X-ray image of the curved sectional area SA is produced.

Accordingly, while a basic X-ray CT method is executed wherein the rotary arm 3 is rotated with its center 3 a fixed, simultaneously a conical X-ray beam 1a with a fixed width is locally radiated, and also a panoramic X-ray image can be produced.

In FIG. 8, like FIG. 7, the rotary arm 3 is rotated at a constant velocity with its center 3a and the width of the conical X-ray beam 1a fixedly supported so as to form the specific region Q. The X-ray generator 1 radiates only the ortho-conical X-ray beam 1b orthogonal to the curved sectional area SA through a slit window 8a by controlling synchronous transferring of a radiation control slit 8 in the direction orthogonal to the conical X-ray beam 1a depending on the change of rotational angle of the arm 3. Accordingly only the partial X-ray projection image projected on the two-dimensional X-ray image sensor 2 is extracted, the extracted image is processed, a three-dimensional distribution information of an X-ray absorption coefficient of the dental arch S is taken out as an image information, and the panoramic X-ray image of the dental arch S is produced.

The specific region may be preferably in the area of the curved sectional area SA along the dental arch or inside of the bow-shape of the area. Most preferable position is inside of a bow-shape of the area and also on the axis of symmetry of the dental arch. In case of obtaining a panoramic X-ray image of one side of a jaw or a partial local region, the center of the specific region may be in the curved sectional area.

Thus, in addition to the effect of FIG. 7, the X-ray exposed dose of the object can be reduced as the rate that a conical X-ray beam is changed to an ortho-conical X-ray beam.

Figure 9A:
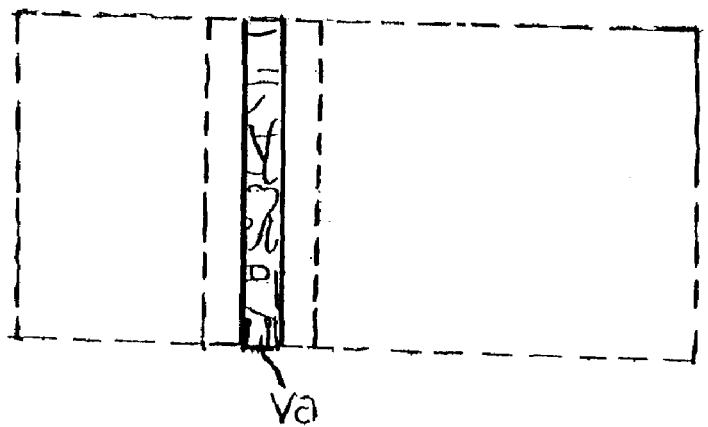
FIG. 9a is a partial X-ray image of a dental arch and FIG. 9b explains a panoramic X-ray image of a dental arch.
Figure 9B:
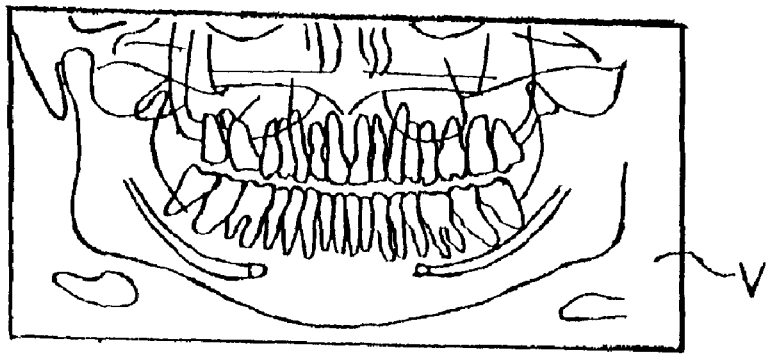

FIG. 9a shows a partial panoramic X-ray image Va produced from a partial X-ray projection image further extracted from the X-ray projection image produced on the two-dimensional X-ray image sensor 2 or from the partial X-ray projection image directly projected on the two-dimensional X-ray image sensor 2 after backprojection processing and extracting the three-dimensional distribution information of an X-ray absorption coefficient according to the present invention. FIG. 9b shows an example of a panoramic X-ray image V produced by aligning and combining the X-ray partial panoramic X-ray image Va.

In the embodiments explained above, the panoramic image layer SB of the dental arch S linking the center of articulation plane of teeth is selected as a sectional image layer to produce panoramic X-ray images of the dental arch but the invention is not limited to this embodiment. To observe the periodontal ligament situation, for example, the sectional image layer closer to a root of the dental arch S compared to the panoramic image layer SB is selected or sectional image layers are accordingly selected depending on the kinds of panoramic X-ray image.

Next, the X-ray CT apparatus of the present invention will be described hereinafter.

Figure 10:
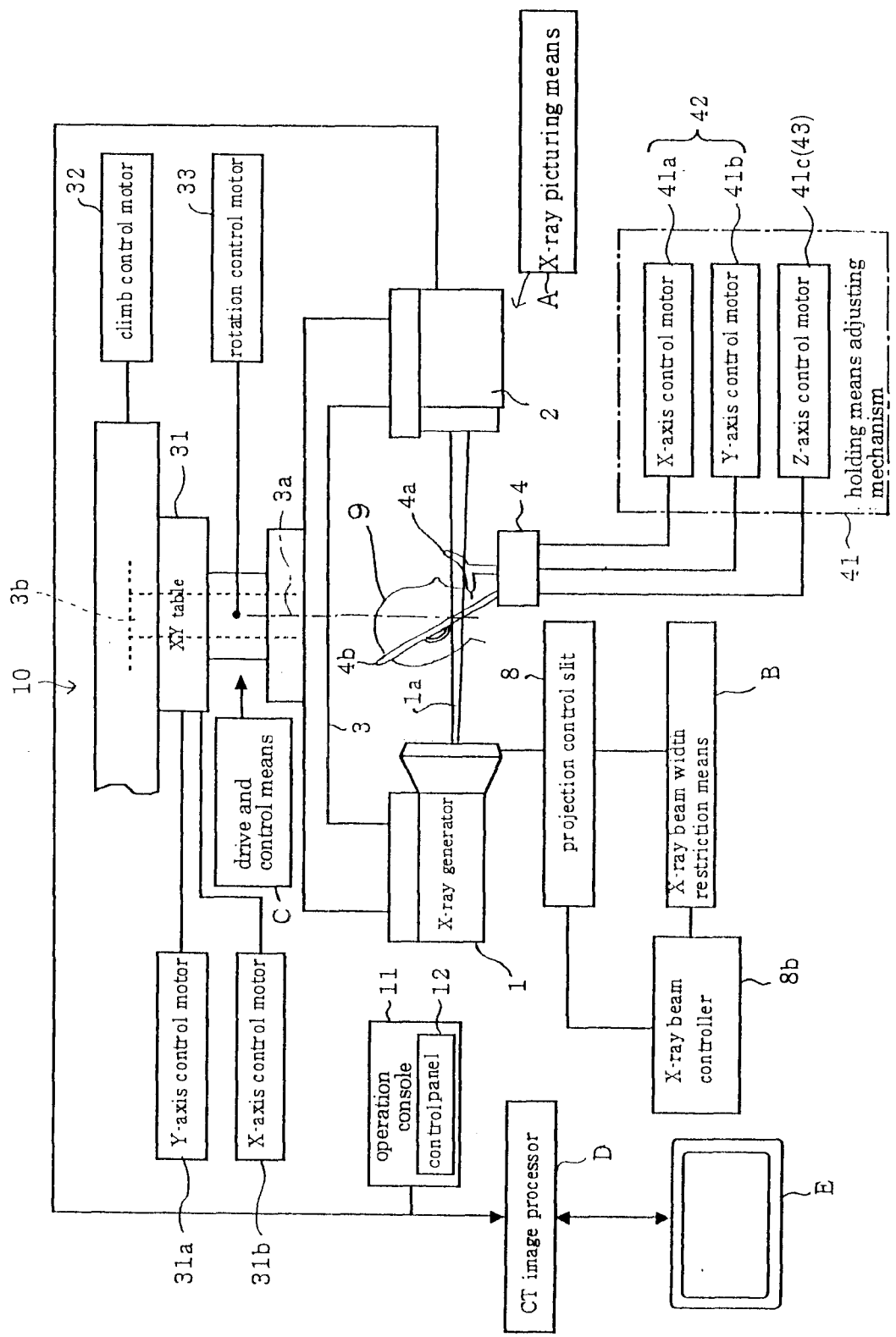
FIG. 10 shows basic construction of an X-ray CT apparatus of the present invention.

FIG. 10 is a block diagram showing a rough construction of the X-ray CT apparatus of the present invention.

The x-ray CT apparatus 20 is comprised of projection means A, an X-ray beam width restriction means B, drive and control means for a rotary arm C, an image processor D, a display E, object holding means 4, a main frame 10, an operation console 11, a control panel 12 and so on. The projection means A and the drive and control means for a rotary arm C are called turning means in all.

The projection means A is provided with a rotary arm 3 and the arm 3 is located such that the X-ray generator 1 and the two-dimensional X-ray image sensor 2 are opposing and suspending.

The X-ray generator 1 is provided with the X-ray beam width restriction means B having a radiation control slit 8 and an X-ray beam controller 8b. The X-ray beam projected from an X-ray tube is adjusted by the X-ray beam width restriction means B and a conical X-ray beam 1a or an ortho-conical X-ray beam 1b with a desired beam width is designed to be radiated.

A well-known two-dimensional X-ray image sensor 2 is used wherein an optical fiber element for transmitting an optical image is provided on a MOS image sensor arranging a photodiode two dimensionally and further a scintillator layer for converting an X-ray to a visible ray is formed thereon.

The rotary arm 3 is provided with an XY table 31, a climb control motor 32, and a rotation control motor 33. The center 3a of the arm 3 can be set in X, Y direction by controlling an X-axis control motor 31a and a Y-axis control motor 31b. The arm 3 is designed to go up and down by driving the climb control motor 32 and to be rotated around the object R by driving the rotation control motor 33 at a constant velocity in case of roentgenography. The climb control motor 32 comprises an adjusting means of up and down position of the arm 3.

The center 3a of the rotary arm 3, namely a rotary axis, is provided vertically, the arm 3 is rotated horizontally, and the conical X-ray beam 1a is horizontally and locally radiated. Therefore, the apparatus can be constructed as a vertical type, which requires a little occupied floor area.

The rotation control motor 33 is comprised as rotation driving means of the rotary arm 3, uses a motor such as a servo motor freely controllable its rotary speed and rotary position, and is positioned so as to be directly connected to the center 3a of the rotary arm 3 by the axis.

Therefore, the arm 3 can be rotated at a constant velocity or at variable velocity and its position can be known along a time axis. It is convenient to take out an X-ray projection image by the two-dimensional X-ray image sensor 2 at an exact timing, there is no core deflection, and thereby the X-ray CT method of the present invention can be effectively executed.

The center 3a of the rotary arm 3 is provided with a hollow 3b. All the associated parts provided for the center 3a should be hollow aperture respectively so as to provide the hollow 3b. For example, a servomotor with a hollow axis can be used as the rotation control motor 33 for this purpose.

The hollow 3b is formed for disposing a connecting line between the X-ray generator 1 and the two-dimensional X-ray image sensor 2 both suspending from the rotary arm 3 and the operation console 11 provided at the main frame 10 side.

When an electrical wiring is connected for a rotation part, its wiring method becomes a problem. However, when the electrical wire is disposed through the center 3a of the rotary arm 3, affect such as twisting caused by rotation can be minimized and further such an arrangement has an aesthetic preferable effect.

The driving and controlling means for a rotary arm C is constructed by combining the XY table 31 (namely a fixing means), the climb control motor 32 and the rotation control motor 33 in this embodiment. However, the invention isn't limited to such a construction. As a most simple construction, the center 3a of the rotary arm 3 can be set at an optional position by operating a manual handle.

The XY table 31 for horizontally moving and setting the center 3a of the rotary arm 3 is provided for positioning the center 3a at the center of the local region P or at the center of the specific region Q in the object R to be radiographed by an X-ray CT. When the object holding means 4 with a holding means adjusting mechanism 41, will be described hereinafter, is provided, such an arrangement can be done at the object side. Therefore, such an XY table 31 isn't always required.

The object R (here a human head is used as an example) places his lower jaw on a chin rest 4a of the object holding means 4, inserts the tips of ear rods 4b in both conchae, thereby the head is properly positioned. The object holding means 4 is provided with the holding means adjusting mechanism 41 having an X-axis control motor 41a, a Y-axis control motor 41b, and a Z-axis control motor 41c. The vertical position is adjusted according to the height of the object R and the longitudinal position is set so as to locate the object R at an appropriate position for projection.

The object holding means 4 is placed on the combined table (not shown) of an X-axis linear movable table, a Y-axis linear movable table, and a Z-axis linear movable table provided with the X-axis control motor 41a, the Y-axis control motor 41b, and the Z-axis control motor 41c respectively. These linear movable tables are comprised of a well known cross roller guide and a combination of a regular bearing and a guide respectively and can linearly move accurately. Although rack and pinion system, a ball screw system, and a normal screw axis system can be used to move these tables, accurately positioning system is desirable.

An object horizontal position adjustment means 42 is comprised of the X-axis control motor 41a and the Y-axis control motor 41b with such linear movable tables and driving systems and an object vertical position adjustment means 43 is comprised of the Z-axis control motor 41c.

Thus, the object horizontal position adjustment means 42 for freely setting the horizontal position of the object R and the object vertical position adjustment means 43 provided for freely setting the vertical position of the object R are provided. The height of the object holding means 4 can be adjusted at the height of the object R. Further, it is advantageous to adjust the center Pa of the local region P in the object R to the center 3a of the rotary arm 3.

As mentioned above, if the rotary arm 3 is provided with the XY table 31 for moving the center 3a thereof and the climb control motor 32, the object horizontal position adjustment means 42 isn't always required. However, sometimes it may be advantageous that the rough position of the object R is adjusted by the object horizontal position adjustment means 42 and the object position adjustment means 43 and then fine adjustments are done by the XY table 31 and the climb control motor 32 provided for the rotary arm 3, thereby both may be provided.

As an adjusting means for the object R, other than the above-mentioned, a chair on which the object R (here it is a patient having the head) and together the object holding means 4 may be moved so as to be positioned. In such a case, the position of the patient can be gently positioned while sitting on a chair.

The image processor D includes an arithmetic processor operating an image process analysis at high speed and the three-dimensional distribution information of an X-ray absorption coefficient in the object through which an X-ray passes is calculated by executing a predetermined arithmetic operation after pre-processing the X-ray projection image produced on the two-dimensional X-ray image sensor 2. Then an optional sectional image and a panoramic X-ray image of the projected local region P are shown by the display E and they are stored in a storage medium as an image information if necessary.

The image processor D may calculate during the picturing, or may calculate only after the picturing as necessary.

The main frame 10 is a structure supporting the whole apparatus 20 and will be detailed hereinafter. The operation console 11 controls the whole apparatus 20 and executes several controls and commands receiving an input from the control panel 12.

The control panel 12 is provided for inputting necessary data for the apparatus 20 and operating procedures and will be detailed hereinafter.

Figure 11:
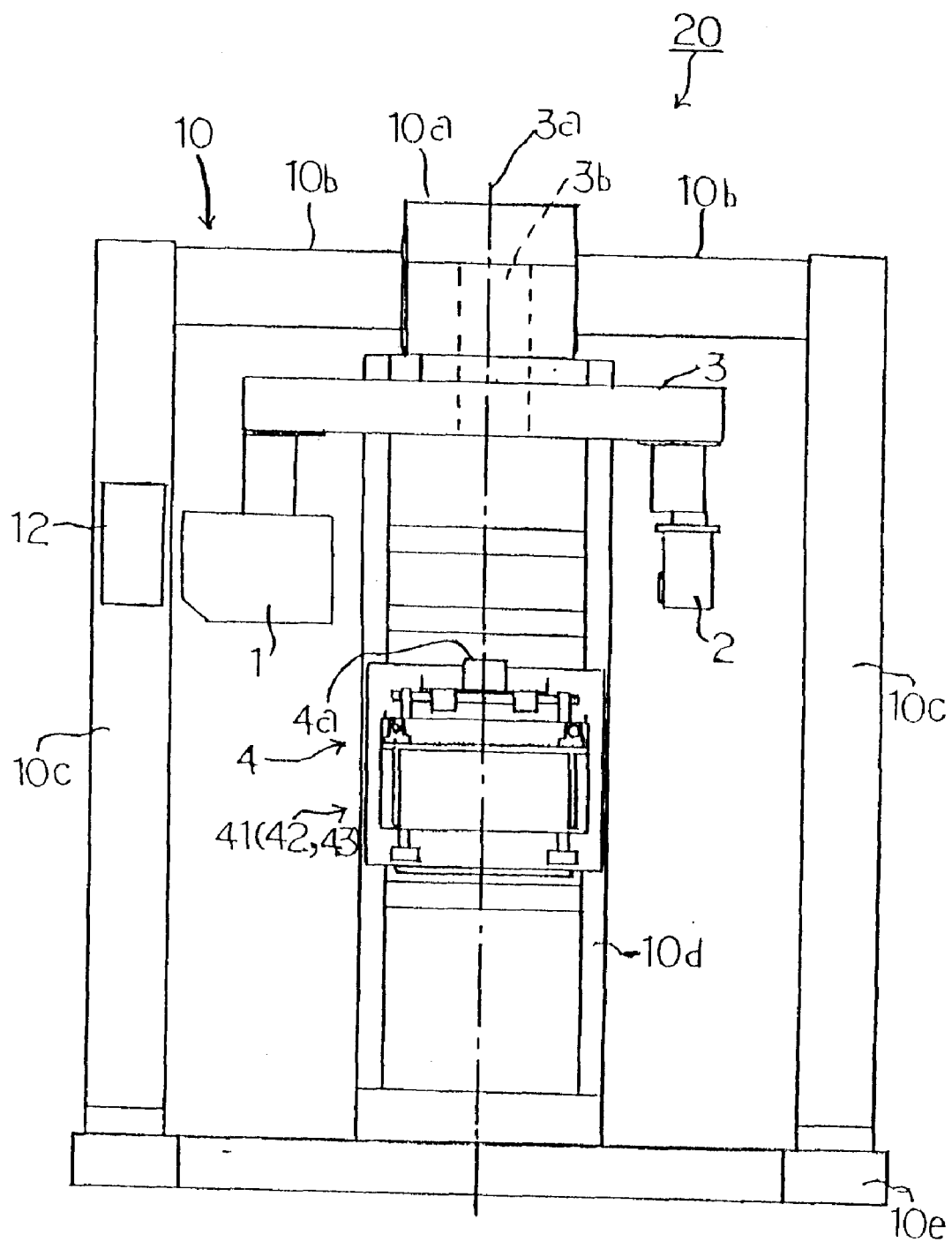
FIG. 11 is an external front view of an example of an X-ray CT apparatus of the present invention.
Figure 12:
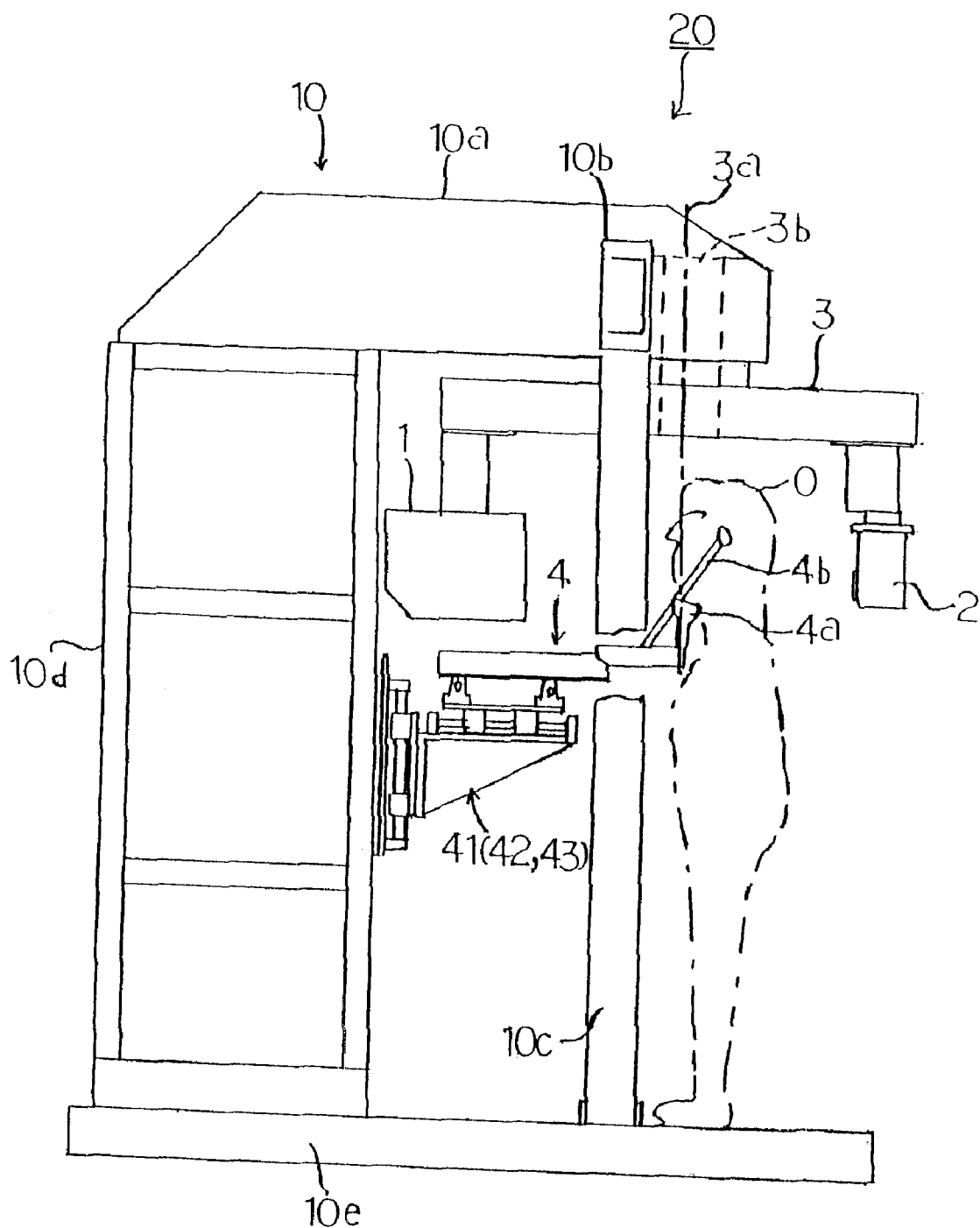
FIG. 12 is an external side view of an example of an X-ray CT apparatus of the present invention.

FIG. 11 is an external front view of an example of an X-ray CT of the present invention. FIG. 12 is its external side view. The members already explained are referenced as the same reference numbers and characters and their explanations are omitted hereinafter.

The X-ray CT apparatus 20 is provided with the main frame 10, which is a highly rigid structure like a gate as a support for the whole apparatus.

The main frame is comprised of an arm 10a rotationally supporting the rotary arm 3 suspending the X-ray generator 1 and the two-dimensional X-ray image sensor 2 opposing each other, a pair of lateral beams 10b for fixing the both sides around the rotary arm supporting area of the arm 10a to prevent deflection caused by rotation of the arm 3, a pair of vertical beams 10c for supporting the lateral beams 10b, a column 10d for fixedly placing the arm 10a, and a base 10e on which the column 10d and the pair of vertical beams 10c are placed and which is a base of the apparatus 20.

These members comprising the main frame 10 are made of highly rigid steel and are strong for deformation by appropriately providing a diagonal brace and a reinforcing material for angles. Especially the arm 10a for rotationally supporting the rotary arm 3 is a highly rigid structure by itself, further, the pair of lateral beams 10b, the pair of vertical beams 10c are provided at the rotary support so as to prevent rotary deflection. Therefore, the center 3a of the rotary arm 3 doesn't move when rotating.

Thus, the main frame 10 is preferable for an X-ray CT apparatus especially requiring no deflection because it is a structure without causing deflection caused by the rotary arm 3.

The main frame 10 may not be provided with the lateral beam 10b and the vertical beam 10c if it is a rigid structure.

The control panel 12 is provided at the surface of anti-column 10d side of one of the vertical beams 10c of the main frame 10 and where the operator can easily operate while standing.

Figure 13:
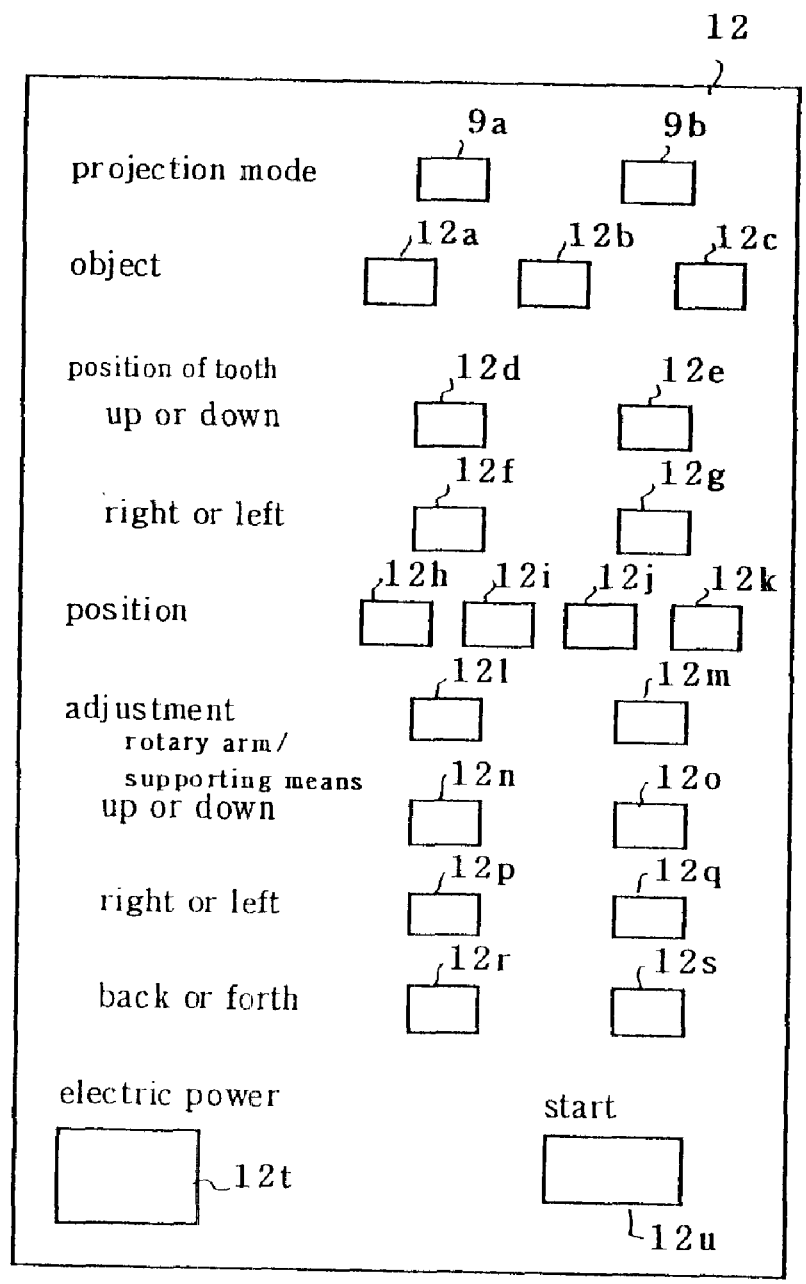
FIG. 13 is a front view showing a control panel of an X-ray CT apparatus of the present invention.

FIG. 13 is a front view showing the control panel of the X-ray CT apparatus of the present invention.

The control panel 12 is provided with a selection switch 9 for selecting the projection mode of the X-ray CT apparatus. The switch 9 is comprised of a partial CT projection mode switch 9a and a panorama projection mode switch 9b for exclusively switching each other. When the partial CT projection mode switch 9a is operated, an optical sectional image of the local region is produced by a normal X-ray CT. When the panorama projection mode switch 9b is operated, a panoramic X-ray image of the dental arch S is produced by the X-ray CT for producing a panoramic X-ray image.

As mentioned above, according to the X-ray CT method of the present invention, when a panoramic X-ray image is produced, the center 3a of the rotary arm 3 may be fixed at a predetermined position as it is and its rotary angle and the width of a conical X-ray beam are changed and slit control is executed. Therefore, the X-ray CT apparatus, which can produce both a panoramic X-ray image and a sectional image, can be simply constructed.

In stead of providing such a selection switch 9, the sensor used for the two-dimensional X-ray image sensor 2 may be a cassette type and a different cassette is prepared for a normal X-ray CT and for a panoramic X-ray image producing X-ray CT. And the partial CT projection mode and the panoramic X-ray projection mode may be changed by exchanging the cassettes.

Furthermore, as necessary, this selection switch 9 may have more alternatives and is usable for selecting various patterns to set the specified angle for producing sectional images distinctive of the present invention.

Selection switches for an object 12a, 12b, 12c are provided under the selection switch 9. These switches 12a, 12b, 12c are used by combining with selection switches for positioning a tooth 12d–12g provided thereunder and used for positioning the object holding means 4 at an appropriate position (see FIG. 10) according to the projection mode. The switch 12a is operated when the object R is a small child, the switch 12b is operated for an average child, and the switch 12c is operated for an adult.

The switches 12d, 12e are used for selecting whether the local region P to be projected is an upper jaw or a lower jaw. When the switch 12d is operated, an upper jaw is selected and when the switch 12e is operated, a lower jaw is selected. The switches 12f and 12g are for selecting right or left of the local region P. When the switch 12f is operated, a left jaw is selected and when the switch 12g is operated, a right jaw is selected.

The position switches 12h–12k thereunder are for selecting further detailed position of the local region P to be projected. When the switch 12h is operated, the first tooth and the second tooth on the basis of the axis of symmetry Lo of the dental arch S are selected. The third and the fourth teeth are selected when the switch 12i is selected, the fifth and the sixth teeth are selected when the switch 12j is operated, and the seventh and the eighth teeth are selected when the switch 12k is operated.

The adjustment switches 12l–12s are for adjusting the position of the rotary arm 3 or the position of the object holding means 4.

The rotary arm 3 is selected as an adjustment object when the switch 12l is operated, the supporting means for the object 4 is selected when the switch 12m is operated.

When the switch 12l is operated and also switches 12n and 12o are operated, the climb control motor 32 is driven and the rotary arm 3 goes up and down. When the switches 12p and 12q are operated together with the switch 12l, the X-axis control motor 31a is driven and the rotary arm 3 moves laterally. When the switches 12r, 12s are operated together with the switch 12l, the Y-axis control motor 31b is driven and the rotary arm 3 moves back and forth.

When the switch 12m is operated and switches 12n and 12o are also operated, the Z-axis control motor 41c of the holding means adjusting mechanism 41 is driven and the object holding means 4 goes up and down. When the switches 12p and 12q are operated together with the switch 12m, the X-axis control motor 41a is driven and the object holding means 4 moves laterally. When the switches 12r and 12s are operated together with the switch 12m, the Y-axis control motor 41b is driven and the object holding means 4 moves back and forth.

An electric power switch 12t provided at the bottom is for turning on and off the electric power of the whole apparatus 20. A start switch 12u is for starting projection.

Thus, the X-ray CT apparatus 20 can be set and operated by the control panel 12.

Figure 14:
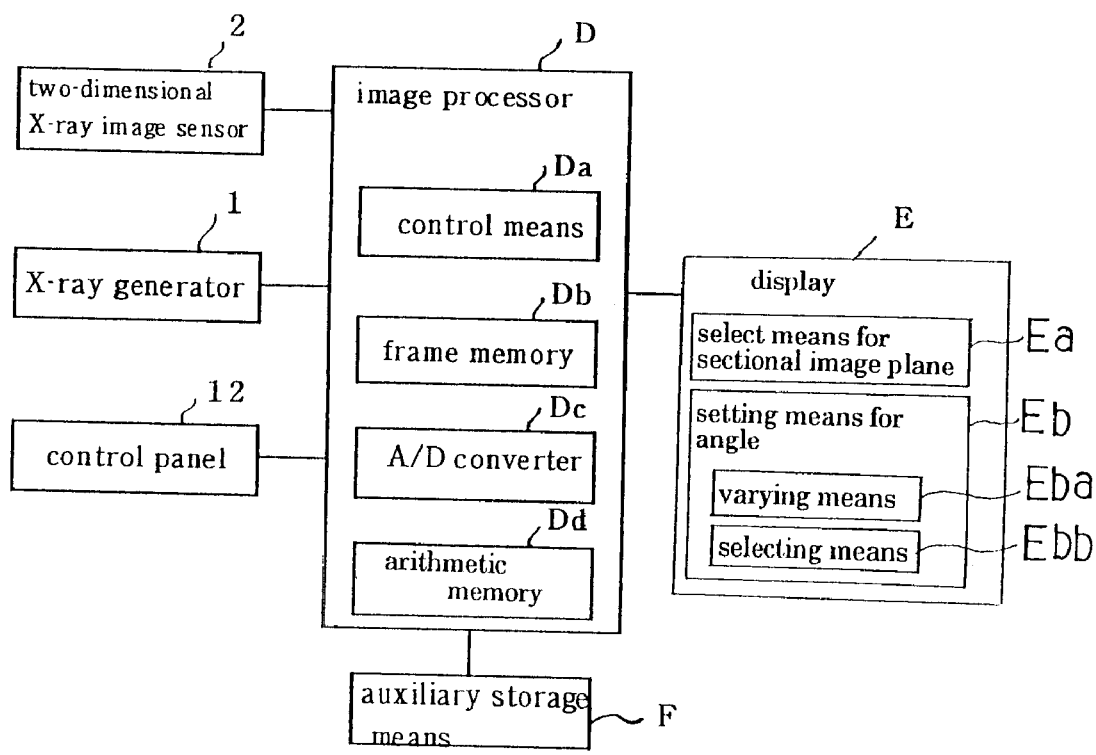
FIG. 14 is a block diagram showing an image processing apparatus of an X-ray CT apparatus according to the present invention.

FIG. 14 is a block diagram showing image processing of the X-ray CT apparatus of the present invention.

The process is executed by an image processor D as a main construction, the X-ray generator 1, the two-dimensional X-ray image sensor 2, the control panel 12, the display E, and an auxiliary storage means F. The image processor D is provided with a control means Da, a frame memory Db as image storage means, an A/D (analog to digital) converter Dc and an arithmetic memory Dd.

Such an image processor D may be comprised of a microprocessor for image processing.

The X-ray projection image data received from the two-dimensional X-ray image sensor 2 is converted to a digital signal by the A/D converter Dc and the converted data is stored in the frame memory Db. A plural image data stored in the frame memory Db are stored in an arithmetic memory Dd, and a predetermined backprojection processing is executed for the stored image data corresponding to the selected projection mode in such a manner that the three-dimensional distribution information of an X-ray absorption coefficient is calculated and an weighted average or an arithmetical average thereof is processed based on the calculated data. Then a sectional image or a panoramic X-ray image is produced.

These images are displayed on the display E, and these data as a three-dimensional distribution information of an X-ray absorption coefficient, sectional images and panoramic X-ray images are stored in the auxiliary storing means F if required. Or, the three-dimensional distribution information of an X-ray absorption coefficient once obtained may be stored with relation to the original projection image data in the frame memory Db.

The display E includes a select means for a sectional image layer Ea to select a sectional image layer and a setting means for an angle Eb to set the specified angle β (see FIG. 1). The setting means for an angle Eb includes a varying means Eba to variably set the specified angle as a projection parameter and a selecting means Ebb to select the angle from the predetermined options as a projection parameter, so that the specified angle can be set by one of these means.

In this display E, the sectional image with respect to the desired sectional image layer seen from the different directions can be sequentially displayed as follows: after the three-dimensional distribution information of an X-ray absorption coefficient is computed, the sectional image layer is specified by means of the selecting means for a sectional image layer Ea and then the specified angle β is set sequentially by means of the setting means for an angle Eb with respect to the set sectional image layer. These selecting means Ea and Eb are called a tomography condition preset means in all.

A partial local projection mode or a panoramic X-ray projection mode is selected by the selection switch 9 and further the select means for a sectional image layer Ea and the setting means for an angle Eb are appropriately selected and set. Accordingly, a direction of a projection lineγ is made same for all the region of the selected image layer or the panoramic image layer or it is changed per region or section, continuously, step wisely, or selectably from prepared plural values, then a sectional image or a panoramic X-ray image of the selected sectional image layer or the selected panoramic image layer seen from the projection line can be obtained by one X-ray CT apparatus.

A hard disc, a magnetic optical disc, and so on can be used as the auxiliary storing means F.

Figure 15:
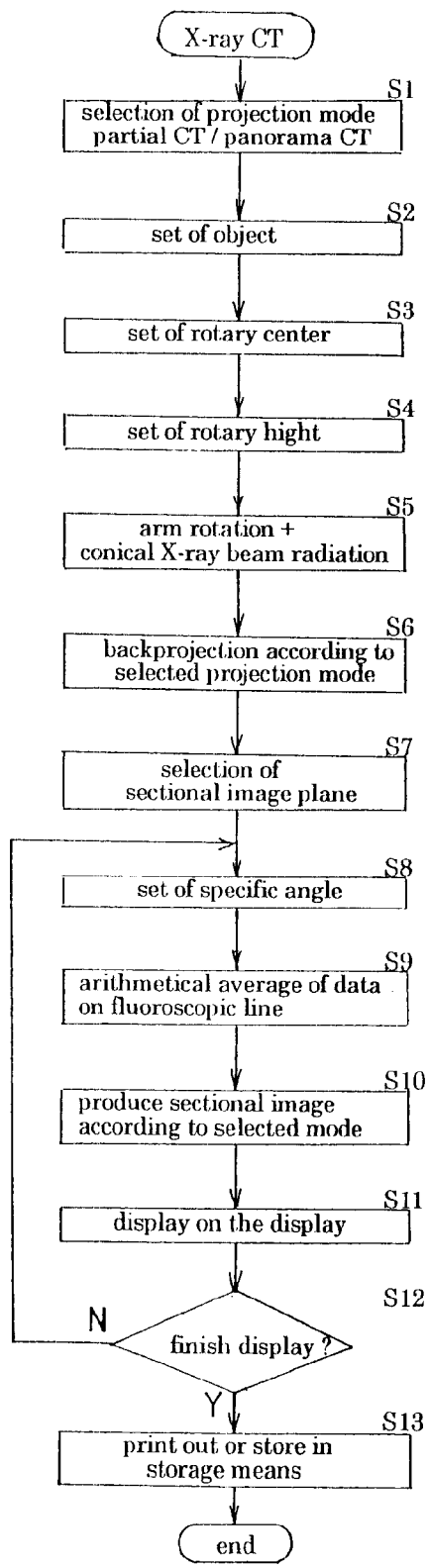
FIG. 15 is a flow chart showing projection procedures of an X-ray CT apparatus of the present invention.

FIG. 15 is a flow chart showing projection procedures of the X-ray CT apparatus of the present invention. Referring to the flow chart, projection procedures will be explained.

The selection switch 9 of the control panel 12 selects the partial CT projection mode or the panorama projection mode (S1). The object R is placed on the chin rest 4a of the object holding means 4 (S2). The center 3a of the rotary arm 3 is set at the center Pa of the local region P of the object R at the partial CT projection mode, and the center 3a is set at the center Qa of the specific region Q of the object R at a panorama projection mode (S3).

Then the height of the rotary arm 3 is adjusted so that the vertical height of the conical X-ray beam 1a locally radiated from the X-ray generator 1 is set in the local region P or the specific region Q (S4). Projection is started and the conical X-ray beam 1a is locally radiated according to the projection mode while the rotary arm 3 is rotated within a fixed angle area corresponding to the projection mode (S5)

Then, as explained in the X-ray CT method, an image processing including backprojection is executed according to the projection mode and the three-dimensional distribution information of an X-ray absorption coefficient is obtained (S6).

Now depending on the projection mode, the sectional image layer of the local region (in case of a panoramic X-ray image, the panoramic image layer in the curved sectional area along the dental arch) is selected by the selecting means for a sectional image layer Ea (S7) provided at the display E and the specified angle β to determine a direction of a projection line is set by the selecting means for a projection line Eb (S8). Depending on this selection and setting, the image processor D computes the arithmetic operation (S9), produces sectional images or panoramic X-ray images (S10) and displays the images onto the display E (S11), of which procedures will be explained hereinafter with respect to FIG. 16.

After this displaying, if an image from another specified angle β becomes necessary, the image corresponding to the newly set angle β is produced and displayed (S12, S8–S11) by setting the angle β by means of the setting means of projection line Eb.

When the display operation is completed, the data is transferred to the printer, or stored in the storage means (S13), if necessary. This is a sequence of a cycle.

Once an X-ray is locally radiated and the three-dimensional distribution information of X-ray absorption coefficient of the local region is obtained and its result is stored, it is possible to watch preferred sectional images or panoramic X-ray images from preferred angles of preferred sectional planes at any time by repeating the procedures S7 to S12 explained above.

Figure 16:
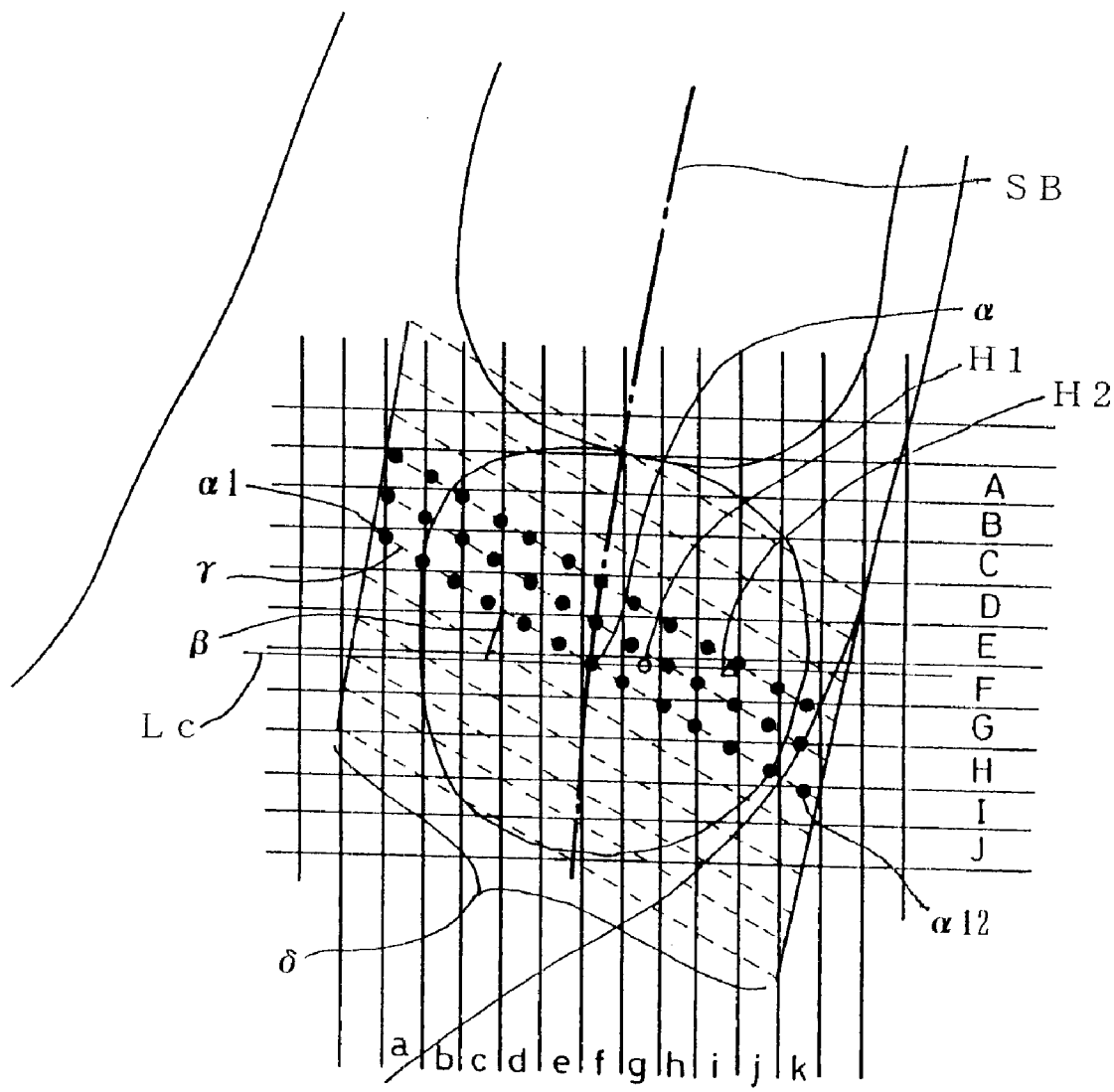
FIG. 16 is a conceptual diagram for explaining the production method of panoramic X-ray images described in FIG. 1 in detail.

FIG. 16 is a conceptual diagram for explaining the production method of panoramic X-ray images for the dental arches described in the FIG. 1 in detail. The members already explained regarding FIG. 1 and 2 are referenced as the same reference numbers and characters and redundant explanations are omitted.

Now the way to compute the arithmetical average, as an example of calculation, will be explained, where an element α among several elements on the panoramic image layer SB of the curved sectional area is used as an example. In order to specify the three-dimensional distribution information of an X-ray absorption coefficient relating to this arithmetical average, the curved sectional area SA in FIG. 18 is divided into several sub areas. Each column of the division is referenced to A to J, each row is referenced to a to k and the combination of a column and a row is referenced to a division Aa, Ab . . . Jk and Jl. The three-dimensional distribution information of an X-ray absorption coefficient obtained in each sub area is displayed as a distribution information Aa, Ab . . . Jk and Jl respectively.

The element α is set as a center, a projection line γ showing a direction of the specified angle β is drawn. Sample points are set within the extracting area δ on the projection line γ with the equal distance taken each other. The total area is divided into twelve sub areas. The points except for the element α are named as α1, α2, . . . α12 respectively.

Next, the distribution information of each sub area to which the sample points α1, α2 . . . and α12 belong, is added, then divided by the total number (in this case 12) to get the arithmetic average.

For example the point a1 belongs to the sub area Ca, α2 belongs to Cb, . . . and α12 belongs to Ik, therefore, an arithmetic average is equal to (distribution information Ca+Cb+Db+Dc+Ed+Ee+Fg+Gh+Gh+Hi+Hj+Ik)/12

If a sample point is positioned exactly on the border line of the sub areas, it is interpreted as belonging to one of the sub areas according to the predetermined rule, for example to the right hand side area or the upper side area, etc. In this example the distribution information Ff relating to the element α which is the center of the extracting area is not considered during the calculation. It could be also included and then the denominator should be 13.

By repeating such procedures with respect to each element α and the projection line γ for the specified angle β, data comprising the sectional images are obtained.

The calculation method isn't limited to the above-mentioned arithmetic average and it may be a weighted average wherein experimentally obtained weighting is done for each distribution data Ca . . . . In such a case, more accurate panoramic X-ray images can be obtained.

Figure 17:
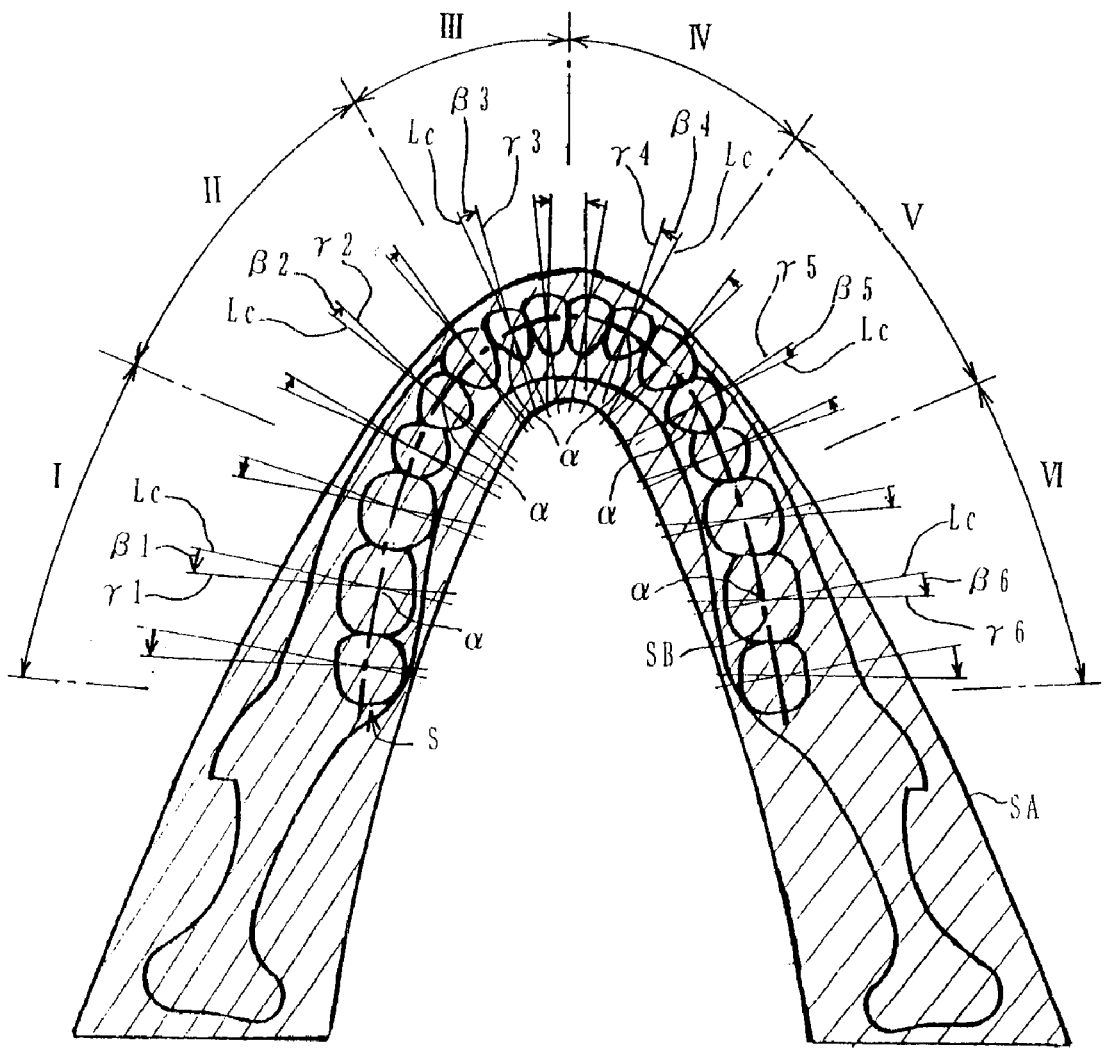
FIG. 17 is a conceptual diagram for explaining another production method of panoramic X-ray images of the present invention.

FIG. 17 is a conceptual diagram for explaining another production method of panoramic X-ray images of the present invention. The setting means of a specified angle for providing a projection line is different from the method shown in FIG. 1.

In this embodiment, the panoramic image layer SB of the curved sectional area SA is divided into plural sections and a direction of a projection line depending on each section is defined. Namely, the panoramic image layer SB is divided into sections depending on diagnosis purposes, the specified angle is different for each section and accordingly the direction of a projection line for a normal line is different.

Also in this embodiment, the panoramic image layer SB of the curved sectional area SA is divided into three sections so as to be symmetric for the center line of a line of symmetry of the curved sectional area SA and six sections I–VI are formed as shown in the figure in which specified angles α1–α6, projection lines γ1–γ6 are defined respectively. In this embodiment, β1=β, β2=β5, β3=4 so as to have the same specified angle t a symmetrical position and accordingly the projection lines γ1, γ2, γ3 are symmetrical for the projection lines γ6, γ5, γ4 respectively.

The direction of such projection line γ corresponds to the line symmetry of the dental arch S or the curved sectional area SA, however, it may completely different in each section. Accordingly different projection lines can be set for each section so that there is high diagnosis freedom.

Figure 18A:
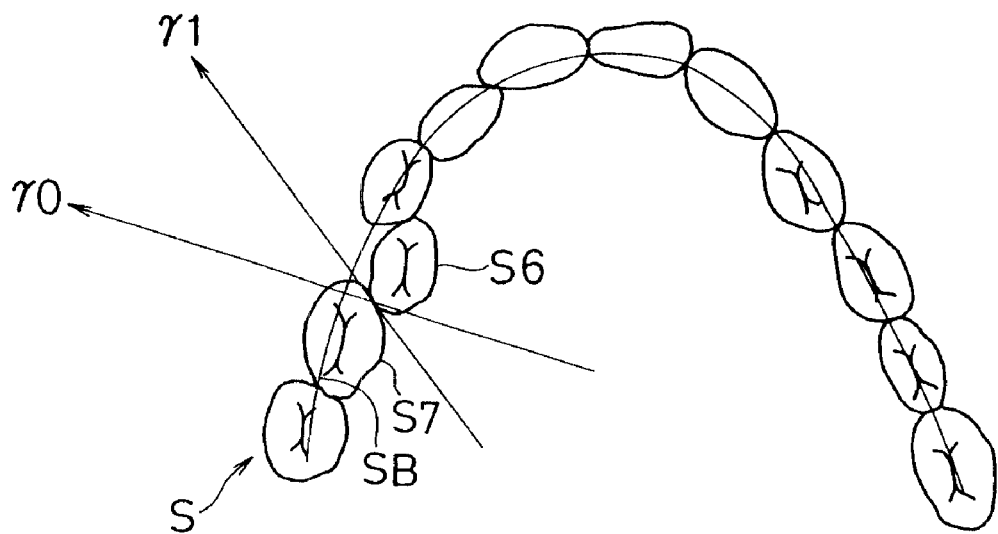
FIG. 18a is a conceptual diagram of a dental arch, which is an object to be examined.
Figure 18B:
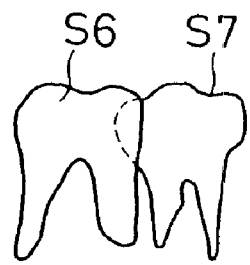
FIG. 18b is a partial panoramic X-ray image of FIG. 18a seen from a direction of a projection line $\gamma 0$, which is a normal line
Figure 18C:
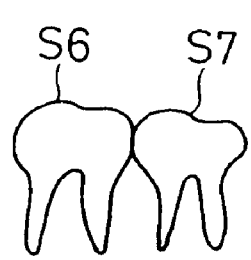
FIG. 18c is a partial panoramic X-ray image seen from a direction of a projection line $\gamma 1$ intersecting a normal line at a specified angle.

FIG. 18 is a conceptual diagram for explaining still another production method of panoramic X-ray images of the present invention, FIG. 18a is a conceptual diagram of a dental arch, which is an object to be examined, FIG. 18b is a partial panoramic X-ray image of FIG. 18a seen from a direction of a projection line γ0, which is a normal line and FIG. 18c is a partial panoramic X-ray image seen from a direction of a projection line γ1 intersecting a normal line at a specified angle.

When the dental arch S is arranged as shown in the figure, the panoramic X-ray image of teeth S6 and S7 is as shown in FIG. 18b wherein images are overlapped and it isn't suitable for an accurate diagnosis if the teeth S6 and S7 are seen from a direction of the projection line γ0, which is a normal line of the panoramic image layer SB. On the other hand, if a projection line γ1 is set so as to be a direction defined by the overlapping part of the teeth S6 and S7, its panoramic X-ray image is as shown in FIG. 18c wherein there are no overlapping parts and it is suitable for diagnosis.

Figure 19A:
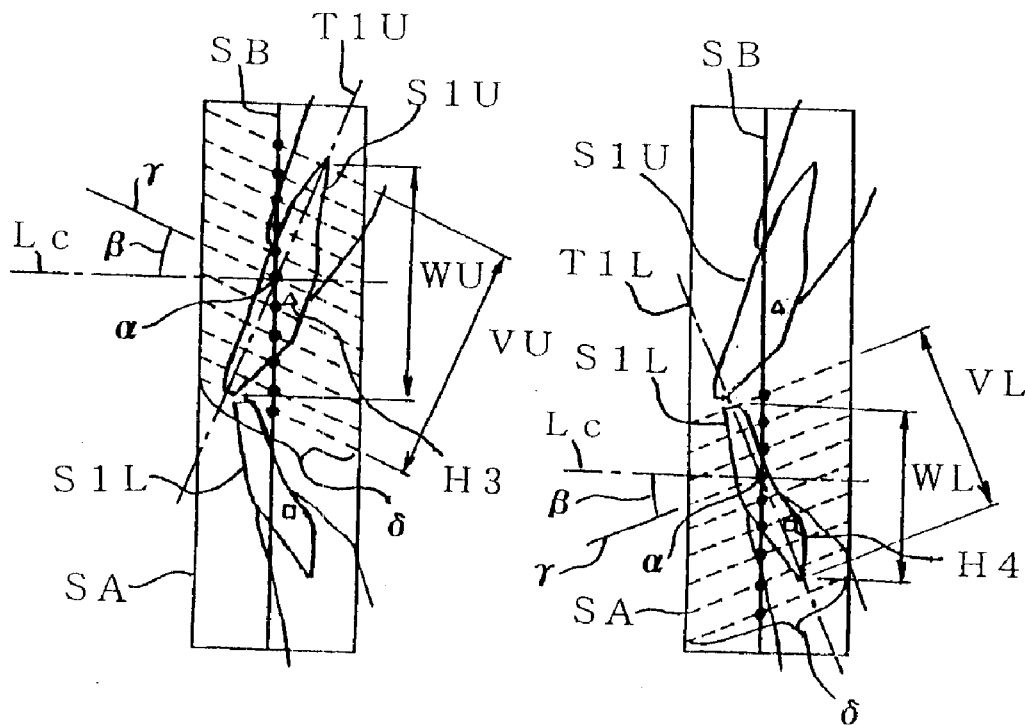
FIG. 19a and FIG. 19b are conceptual diagrams explaining another embodiment of this invention, where the method for producing panoramic X-ray images of the dental arch in locally radiated X-ray CT is introduced.
Figure 19B:
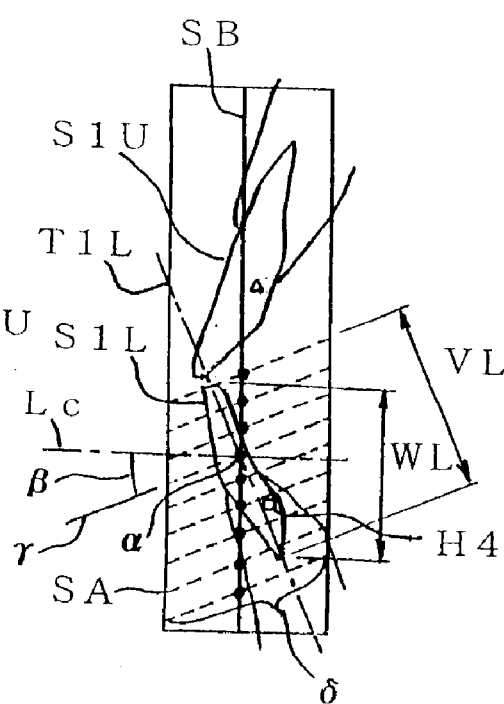
Figure 19C:
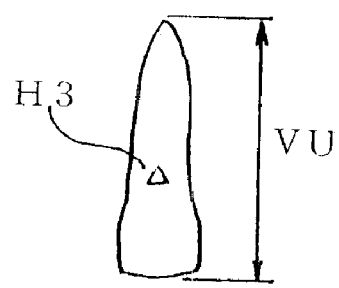
FIG. 19c and FIG. 19d are examples of panoramic X-ray images obtained by this method.
Figure 19E:
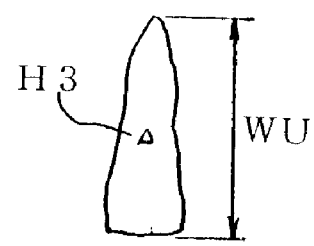
FIG. 19e and FIG. 19f show partial figures of panoramic X-ray images obtained by a conventional method.
Figure 19D:
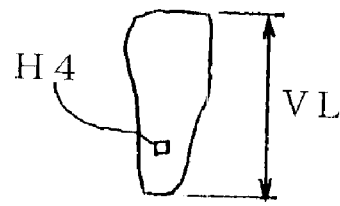
Figure 19F:
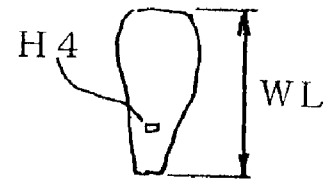

FIG. 19a and FIG. 19b are conceptual diagrams explaining another embodiment of this invention, where the method for producing panoramic X-ray images of the curved sectional image in locally radiated X-ray CT is introduced. FIG. 19c and FIG. 19d are partial vies of the examples of panoramic X-ray images obtained by this method. FIG. 19e and FIG.19f show partial figures of panoramic X-ray images obtained by a conventional method.

The members already explained are referenced as the same reference numbers and characters and their explanations are omitted.

FIG. 19a is a vertical cross section of the front jaw, which is a curved sectional area SA explained in FIG. 24. In this view an upper front tooth S1U and a lower front tooth S1L are visible. FIG. 19a, FIG. 19c and FIG. 19e relate to the upper front tooth S1U, while FIG. 19b, FIG. 19d and FIG. 19f relate to the lower front tooth S1L.

With this method, the projection line γ, namely a normal line, for the upper front tooth S1U, which is set by the specific angle β, is set normal to the rising direction T1U of the upper front tooth S1U. Elements α are set on the panoramic image layer SB of the dental arch as desired and the calculation is executed regarding the elements as in the case of FIG. 16, so that panoramic X-ray images are produced.

This method can be applied to the lower front tooth S1L as well. In this case T1L shows the rising direction of the lower front tooth S1L. The lengths of the upper front tooth S1U and the lower front tooth S1L in the direction of the panoramic image layer SB of the dental arch are WU and WL respectively, while their lengths perpendicular to the projection line γ are VU and VL, respectively. H3 and H4 are foreign objects existing inside the upper front tooth S1U and the lower front tooth S1L, respectively.

FIG. 19c is a partial view of a panoramic X-ray image thus produced for the upper front tooth S1U, while FIG. 19e is a partial view by a conventional method for the same tooth. FIG. 19d is a partial view of a panoramic X-ray image thus produced for the lower front tooth S1L, while FIG. 19f is a partial view by a conventional method for the same tooth. comparing these views it becomes clear that the true length VU of the upper front tooth S1U and that VL for the lower front tooth S1L as well as the positions of the foreign objects H3 and H4 to the true lengths VU and VL respectively are evaluated correctly. On the contrary WU and WL obtained from FIG. 19e and FIG. 19f vary depending on the angles to the rising direction T1U and T1L of the teeth S1U and S1L and are not the correct ones.

Thus, by this method panoramic X-ray images show each tooth most appropriately even if the panoramic image layer of the dental arch, namely the sectional image layer for producing the panoramic X-ray images is fixed.

The specified angle β is fixed for a tooth and varies depending on a tooth because of its different rising direction.

Figure 20A:
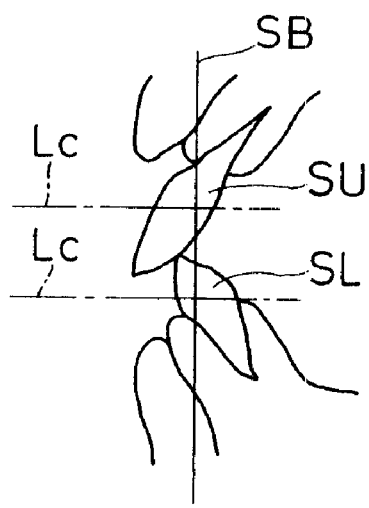
FIG. 20a is a conceptual diagram of the dental arch seen from a direction of a conventional normal line.
Figure 20B:
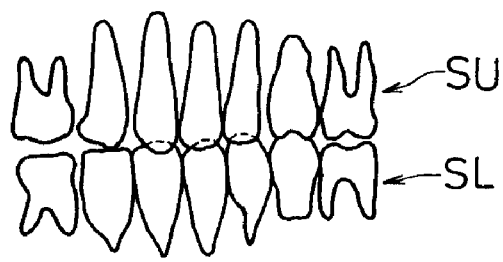
FIG. 20b is a panoramic X-ray image obtained by this method.
Figure 20C:
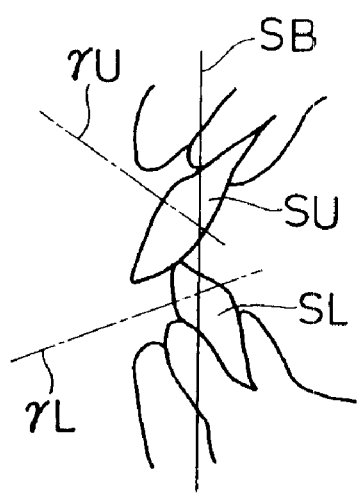
FIG. 20c is a conceptual diagram of the dental arch seen from a direction of a projection line, a normal line into a rising direction of teeth.
Figure 20D:
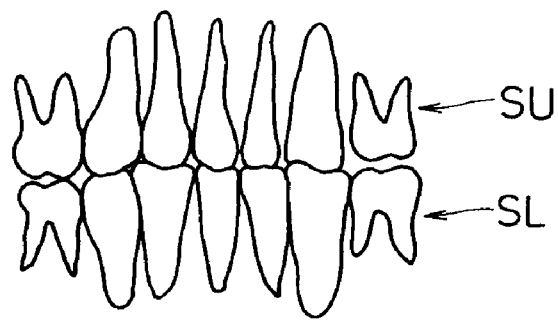
FIG. 20d is a panoramic X-ray image obtained in this case.

FIG. 20 is an example wherein the panoramic X-ray image production method of FIG. 19 is applied for other dental arch, FIG. 20a is a conceptual diagram of the dental arch seen from a direction of a conventional normal line, FIG. 20b is a panoramic X-ray image obtained by this method, FIG. 20c is a conceptual diagram of the dental arch seen from a direction of a projection line of a normal line into a rising direction of teeth, and FIG. 20d is a panoramic X-ray image obtained in this case.

As understood by comparing each view of FIG. 20, when a panoramic X-ray image is produced when the object is divided into an upper jaw and a lower jaw and an upper projection line γU and a lower projection line γL are set to be normal lines into directions of a tooth SU of the upper jaw and the tooth SL of the lower jaw respectively, the length of each tooth is displayed at almost full scale. Even if the upper tooth and the lower tooth are overlapped, a display without such overlapping can be shown and is useful for diagnosis.

Figure 21:
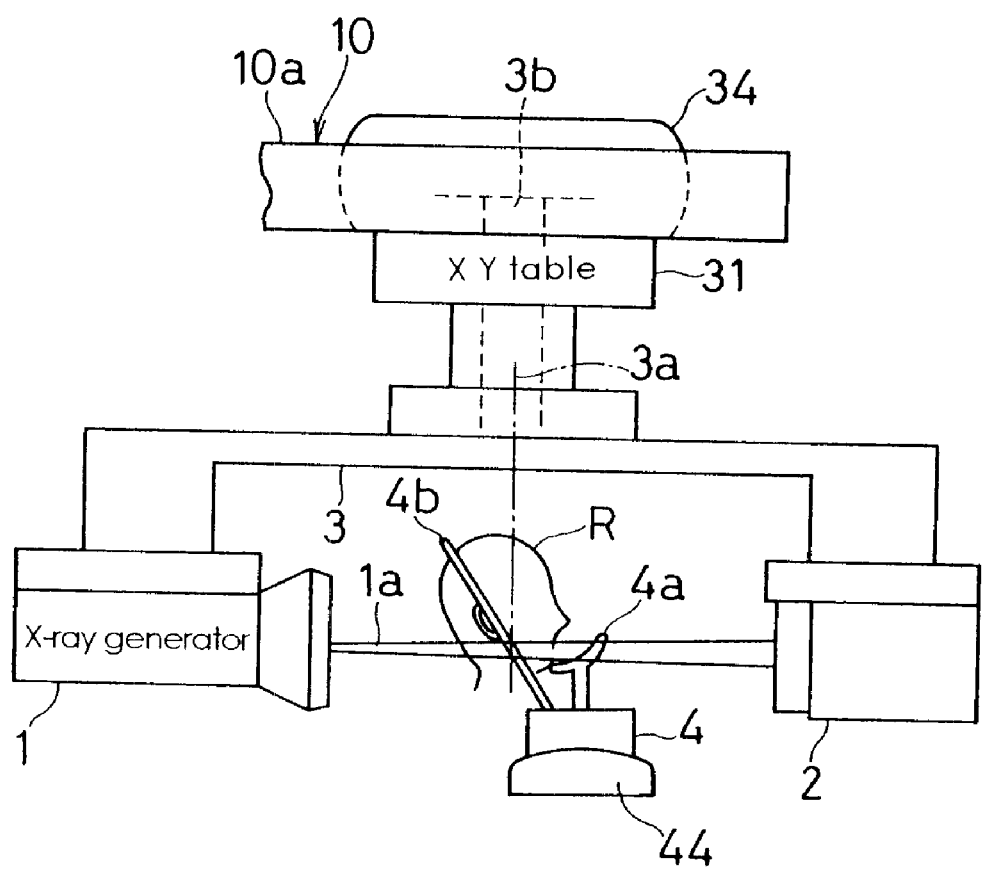
FIG. 21 is a construction view of rotary axis direction setting means and subject supporting direction setting means provided for the X-ray CT apparatus of the present invention.

FIG. 21 is a construction view of rotary axis direction setting means and subject supporting direction setting means provided for the X-ray CT apparatus of the present invention. FIG. 21 shows a construction in which the rotary axis direction setting means 34 and the subject supporting direction setting means 44 are provided for the basic construction of the apparatus of FIG. 1.

The rotary axis direction setting means 34 inclinably supports the entire XY table 31 supporting the rotary arm 3 inclinable for the arm 10a of the main frame 10. It can incline the center 3a of the rotary arm 3, namely the axial direction of the rotary axis, against a perpendicular direction of the object R. The subject supporting direction setting means 44 inclinably supports the object holding means 4 having the chin rest 4a and the ear rods 4b and can incline the object R around the center 3a of the rotary arm 3, namely the axial direction of the rotary axis.

Figure 22A:
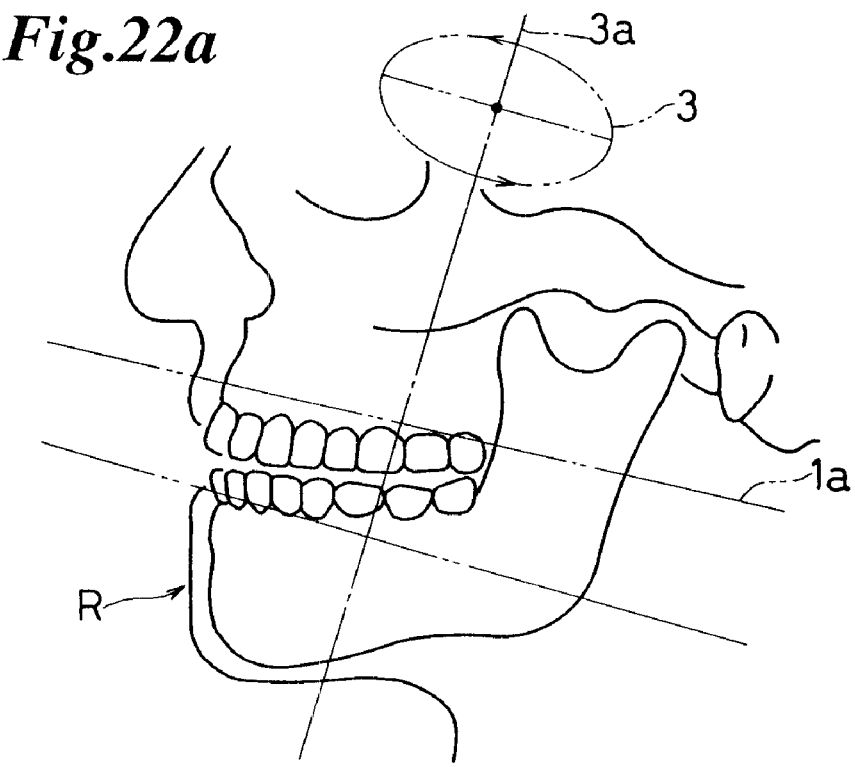
FIG. 22a and FIG. 22b are conception view of an X-ray CT using the rotary axis direction setting means and the subject supporting direction setting means shown in FIG. 21.
Figure 22B:
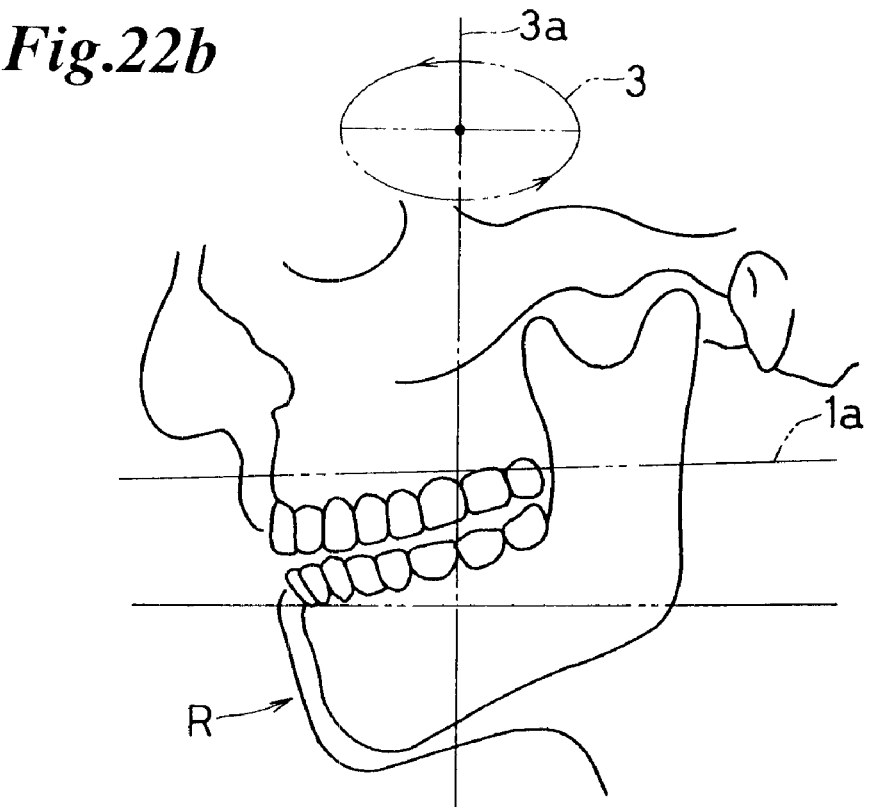

FIG. 22a and FIG. 22b are conception view of an X-ray CT using the rotary axis direction setting means and the subject supporting direction setting means shown in FIG. 21.

As shown in these figures, when the center 3a of the rotary arm 3, namely the axial direction of the rotary arm, is inclined for the object R as shown in FIG. 22a or when the object R is inclined into the axial direction of the center 3a of the rotary arm 3, which is a perpendicular direction, as shown in FIG. 22b, an affecting shadow such as a jawbone can be avoided as well. Further in case of FIG. 22b, the object R which doesn't rotate is inclined so that the construction of the subject supporting direction setting means 44 is simplified.

Figure 23:
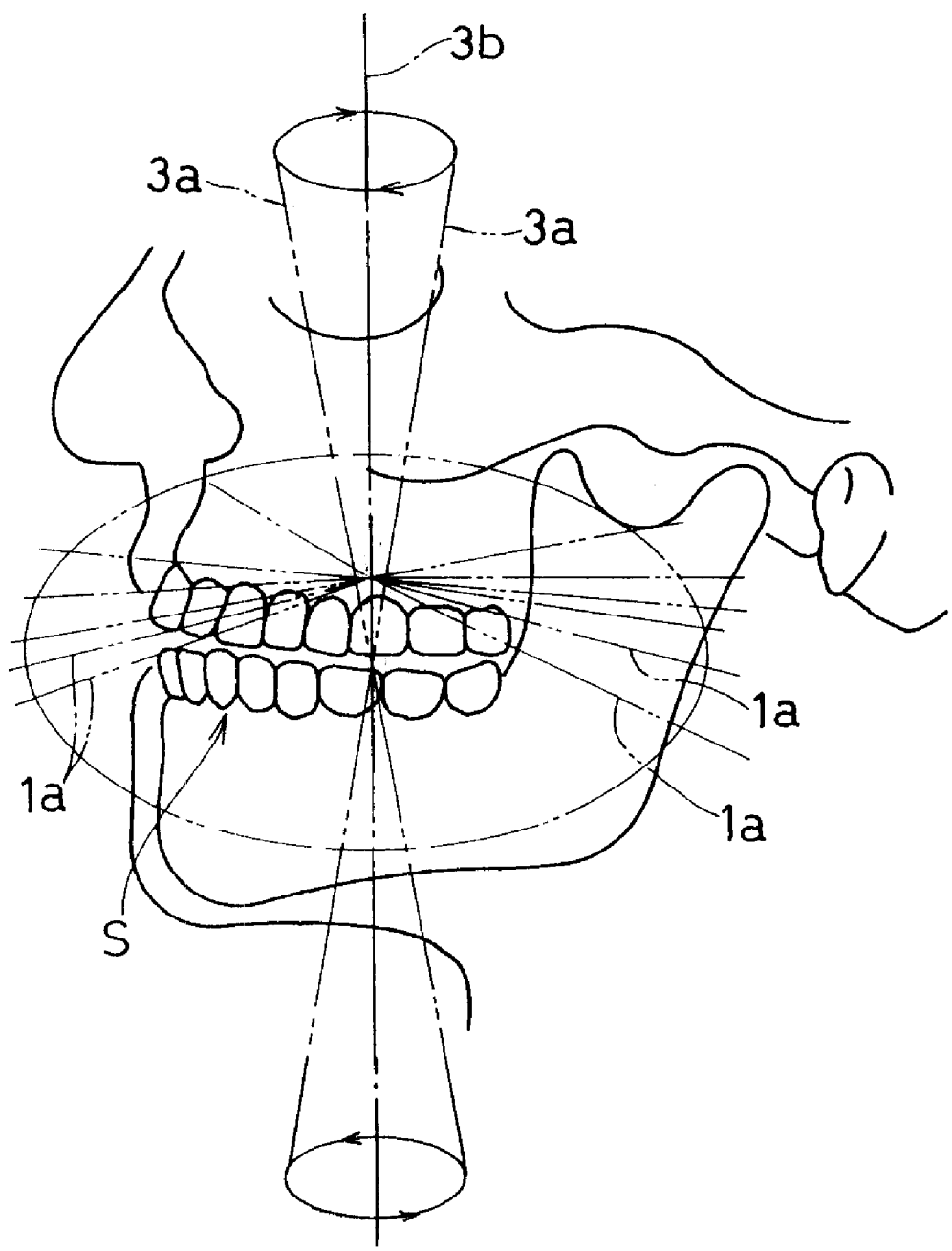
FIG. 23 shows a condition when a rotating axis of a rotary arm executes a precession movement.

FIG. 23 shows a condition when a rotating axis of a rotary arm executes a precession movement. As understood from the figure, a conical X-ray beam 1a is radiated on the object while the rotary arm 3 is turned while making the rotary axis, the center 3a, of the rotary arm 3 a precession movement, namely a grinding movement wherein the rotary center 3a is turned around the precession axis 3b into an arrowed direction while keeping a fixed angle. Comparing to the case when the beam is radiated horizontally or the case wherein the rotary axis is simply inclined, alternative methods are increased for radiating the conical X-ray beam avoiding affecting shadows and correspondence methods to several kinds of affecting shadow are increased. Further in a normal panoramic X-ray projection, not a CT method, X-rays are radiated with about 5 degrees of an angle of elevation so as to remove the affecting shadow. The same method is applied for a CT method so that an X-ray projection image with less affecting shadows can be obtained and a panoramic X-ray image with less affecting shadows can be obtained by a backprojection processing based on the obtained X-ray projection image.

In this embodiment the X-ray CT method and apparatus of the present invention are applied for teeth and a dental arch but the invention is not limited for this field. It can be applied for a mandibular joint, regions of otolaryngology and ophthalmology, a cranium region, a rib and other regions.

Explanation of Fundamental Principle of X-ray CT Method

Figure 25:
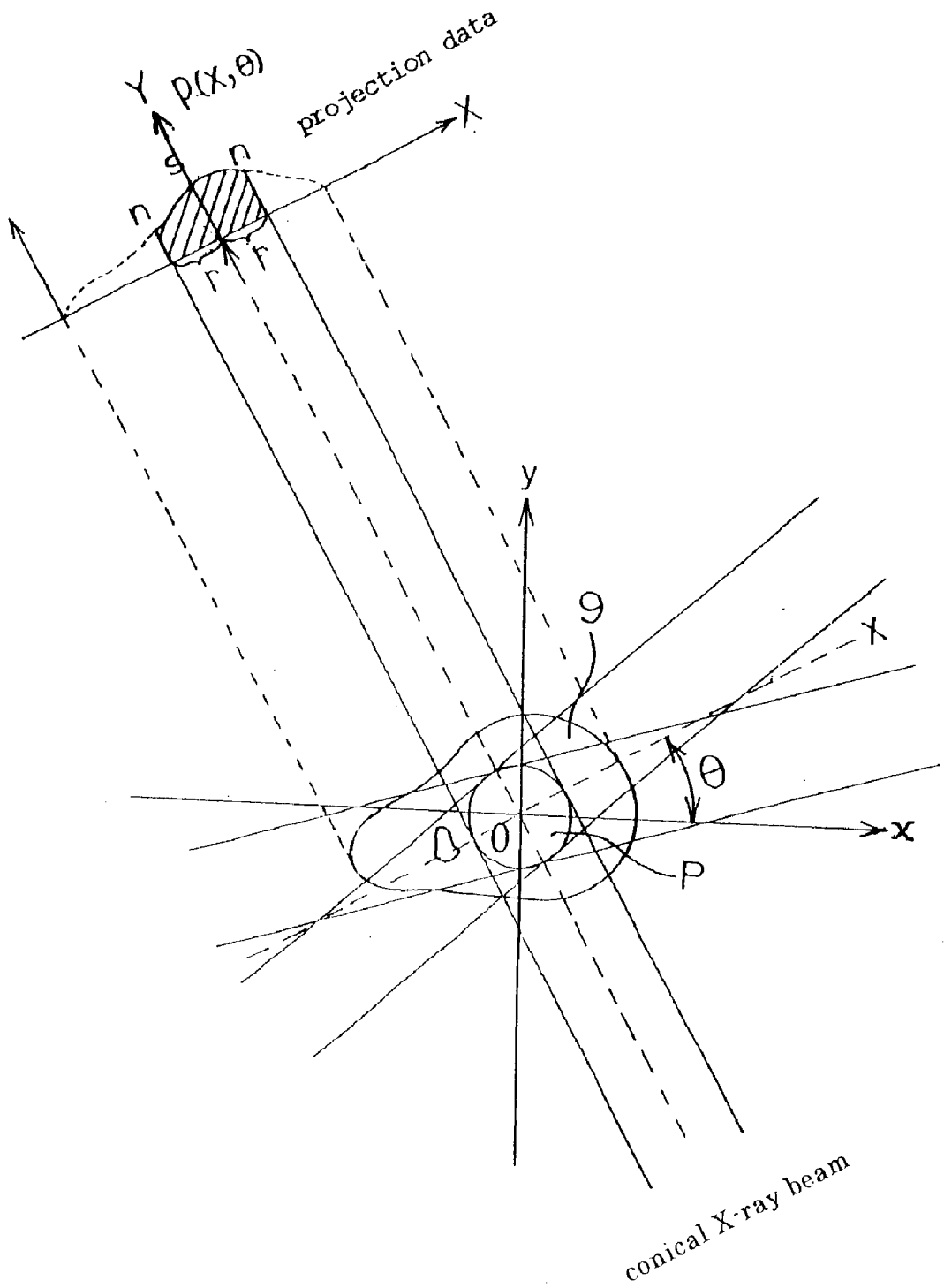
FIG. 25 illustrates a projection data of an X-ray CT method of the present invention.
Figure 29A:
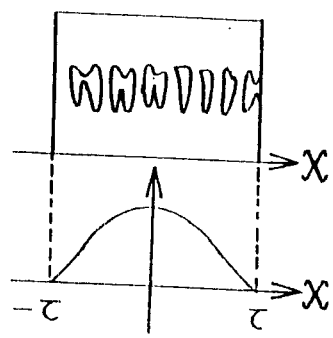
FIG. 29a and FIG. 29b explain an artifact measure for an X-ray CT method of the present invention.
Figure 29B:
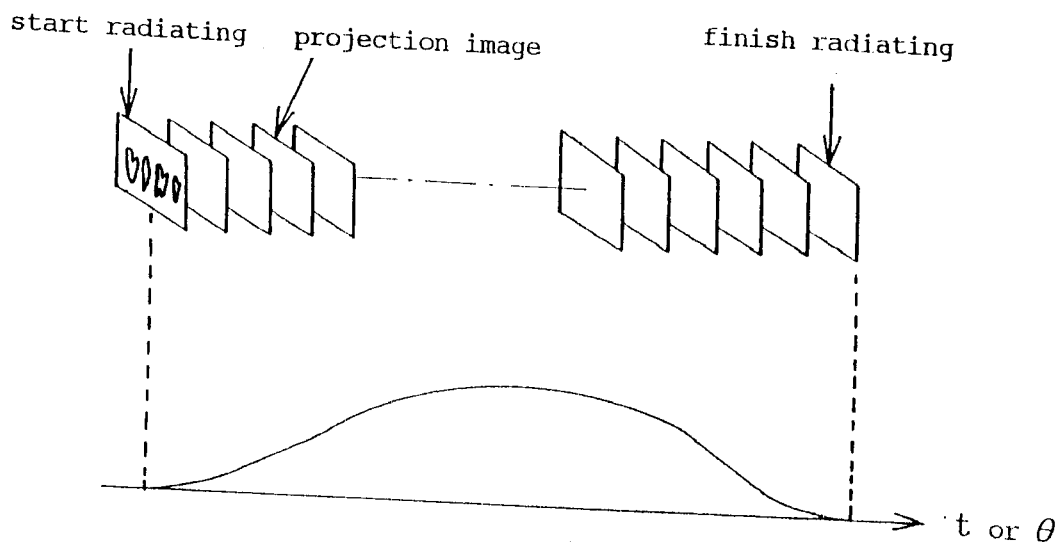
Figure 30:
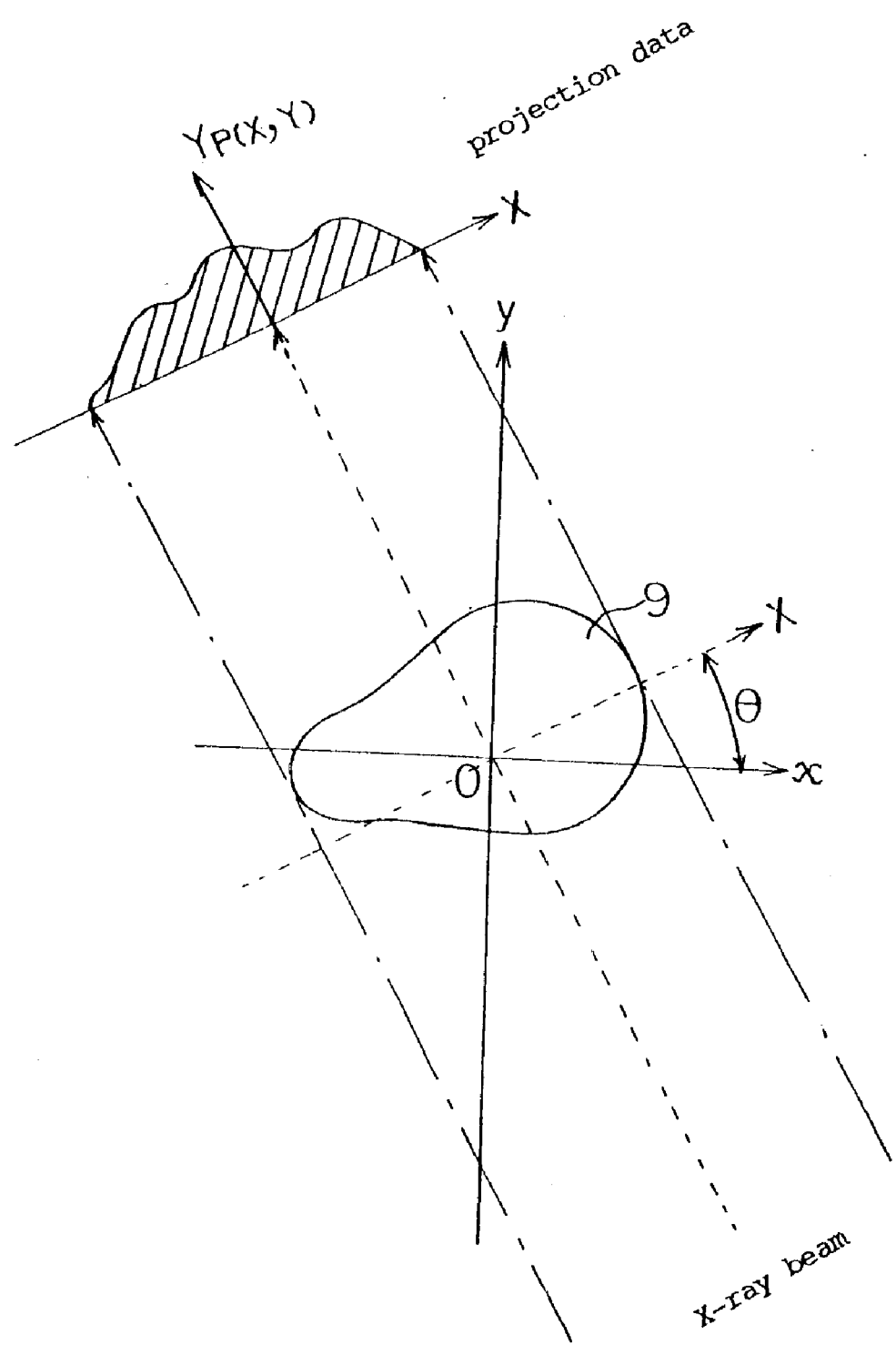
FIG. 30 shows a projection data analyzed by a conventional X-ray CT.

FIG. 25 explains a projection data of the X-ray CT method of the present invention. FIG. 26a, FIG. 26b, and FIG. 26c explain conditional functions used in the X-ray CT method of the present invention. FIG. 27a, FIG. 27b, FIG. 28a, and FIG. 28b explain the fundamental principle of the X-ray CT method for producing a panoramic X-ray image according to the present invention. FIG. 29a and FIG. 29b explain an artifact measure of the X-ray CT method of the present invention. FIG. 30 explains a projection data analyzed by a conventional X-ray CT. FIG. 31 shows arithmetical expressions used for a conventional X-ray CT method.

FIG. 32 shows arithmetical expressions used for the X-ray CT method of the present invention. FIG. 33 shows arithmetical expressions used for the X-ray CT method for producing a panoramic X-ray image according to the present invention. From these figures an X-ray CT method using a conical X-ray beam will be considered.

Conventional X-ray CT Method

When an object R is positioned on an x, y coordinate system, an X-ray beam is irradiated on all around the object R from an inclined angle θ, and a projection data is generated on an XY coordinate system (FIG. 30), the projection data is shown as a (formula 1) of FIG. 31 and the back-projected data is shown as a (formula 2) of FIG. 31 by the convolution method. It has been well known in the conventional analysis method.

A fixed coordinate system xOy is defined on a flat surface including the sectional image layer of the object R, the two-dimensional distribution information of the X-ray absorption coefficient at the coordinate (x, y) is expressed as an original image in the form of a continuous two-dimensional function f (x, y). A parallel X-ray beam is irradiated from every angle direction θ, 0<θ<π, and the intensity of the X-ray passed out of the object R is detected as a projection data.

In this case, as the two-dimensional distribution information f (x, y) of the absorption coefficient in the object R passing an X-ray beam can be obtained by the (formula 3), the integration is calculated and repeated at z-axis direction, namely vertical direction, so that the three-dimensional distribution information of the X-ray absorption coefficient of the object R can be obtained.

The operation called as a data reconstruction by CT includes a two-dimensional Fourier transform method, an one and two-dimensional Fourier transforms method, an one-dimensional Fourier transform method and a convolution method. The above-mentioned convolution method is widely adapted these days to cut operation time drastically. According to the convolution method, only a convolution integral which is a simple sum of products and the back-projection operation, are executed so that the calculation can be executed simply and at high speed.

According to the (formula 4) of FIG. 31, f (x, y) is obtained by a convolution method. The coordinate transformation formula in FIG. 31 is a transformation formula between x, y coordinate of the xOy coordinate and X, Y coordinate of the XOY coordinate.

Normal X-ray CT Method of the Present Invention

According to the normal X-ray CT method of the present invention, comparing to the conventional method, the conical X-ray beam is locally irradiated only on the local region P of the object R as shown in FIG. 25, and its radiant beam width 2r is shown in FIG. 26 and the conditional function as shown in (formula 5) of Fib. 32 is used.

When the conditional function (formula 5) is used, the relation of the (formula 6) in FIG. 32 is formed between the relation of a backprojection data qs (X,θ) of the local region P of the object R, a backprojection data qn (X,θ) other than the local region P of the object R and a whole backprojection data q (X,θ) of the object R. In (formula 6-1) the second term becomes approximately "0" almost all the area between the interval [−r, r].

Namely, the whole projection data of the object R equals to the integration of the projection data of the local region P and the projection data passing through the other area which is an anteroposterior passage of the local region P, so that the relation; q(X,θ)=qs(X,θ)+qn(X,θ) . . . FIG. 32 (formula 7); is formed between each backprojection data and as a result (formula 8) in FIG. 32 is derived.

Therefore, the two-dimensional distribution information fs(x, y) of the X-ray absorption coefficient of the local region P can be obtained when the two-dimensional distribution information fn(x, y) of the X-ray absorption coefficient other than the local region P is subtracted from the two-dimensional distribution information f(x, y) of the X-ray absorption coefficient of the whole object R.

According to the characteristic of the present invention, comparing to the conventional X-ray CT method using a fan-shaped X-ray beam, the beam width in rotary direction of the conical X-ray beam is further minimized than the conventional beam width for radiating the whole object and only the local region which is a part of the object is irradiated. Such an idea can change the conventional idea wherein X-ray beam is irradiated on the whole object for an X-ray CT projection.

The present projection method is based on the idea that the projection data can be always obtained from the local region irradiated by the conical X-ray beam, but the conical X-ray beam temporarily passes out the other area of the object around the local region according to rotation comparing to the local region so that the projection data isn't affected, and in case of backprojection, affect on the projection data other than the local region can be almost ignored. The above-mentioned conditional function (formula 5) expresses such an idea as a formula.

In other words, the two-dimensional distribution information fn(x, y) is an error element and indicates a signal of a rectn function outside of a rects function. While studying the present invention, the inventors of the present invention have found that the two-dimensional distribution information fn(x, y) indicating the error element becomes almost [0]. Accordingly, in the present invention, the error element can be almost disregarded and an image reconstruction can be clearly produced only at a desired local region P.

In case of applying dental projection, the main point is to analyze the shape of a tooth or an implant as a diagnosis object. Such parts have higher X-ray absorption coefficient than the other tissue, therefore, the two-dimensional distribution information fs(x, y) of the X-ray absorption coefficient of such a part becomes larger than the two-dimensional distribution information fn(x, y) of the X-ray absorption coefficient of the other tissue. Consequently more clear sectional image can be produced.

X-ray CT Method for Producing Panoramic X-ray Image of the Present Invention Next, the X-ray CT method for producing a panoramic X-ray image according to the present invention will be studied.

As mentioned above, according to the X-ray CT method of the present invention, it is characterized in that only the local region of the object is locally projected and the sectional image of the local region is obtained. In the present invention, this method is skillfully utilized to produce the panoramic X-ray image of the dental arch, which has been in heavily used in dental surgery.

Conventionally the curved sectional area should be irradiated while transferring the rotary center of the X-ray beam bundle so that the X-ray beam bundle draws a complicated excursion according to the panoramic X-ray image condition in order to produce a panoramic X-ray image. On the other hand, in this X-ray CT method of the present invention, the conical X-ray beam is rotated with the rotary center fixed at a predetermined position. Therefore, it has been a problem how to obtain a panoramic x-ray image by utilizing the apparatus only by achieving rotation with its center fixed, as it is.

In the CT method wherein an fan shaped X-ray is irradiated on the dental arch from 360° all around and the rotary center is fixed at one position during projection, a method has been known that only the X-ray projection data of the dental arch is extracted and reconstructed. However in this method, because the X-ray exposed dose has been large and the imaging apparatus has been large-sized, such a problem has been desired to be solved.

According to the X-ray CT method for producing a panoramic X-ray image of the present invention, in order to produce a panoramic X-ray image of the curved sectional area, a local region is calculated so as to produce a panoramic X-ray image of the curved sectional area. The conical X-ray beam is locally irradiated so as to include only the local region while fixing the rotary center of the conical X-ray beam at the center of the local region and only the partial X-ray projection image by the ortho-conical X-ray beam is extracted from the obtained X-ray projection image of the curved sectional area. Based on the partial X-ray projection image, backprojection is executed to obtain the three-dimensional distribution information of X-ray absorption coefficient and the panoramic X-ray image of the curved sectional area is produced by the obtained three-dimensional distribution information of an X-ray absorption coefficient.

Accordingly, the panoramic X-ray image of the curved sectional area along the dental arch can be obtained by the X-ray CT method.

This basic idea is a developed idea from the X-ray CT method radiating an X-ray beam on the whole object up to the X-ray CT method of a local radiation by a conical X-ray beam. When the local region is selected as above mentioned, the locally projected conical X-ray beam is limitedly radiated on only a prescribed angle area of the curved sectional area for obtaining a panoramic X-ray image. Adequate image data for a panoramic X-ray image can be obtained by extracting the partial X-ray projection image only on the irradiated angle area of the conical X-ray beam. The three-dimensional distribution information of an X-ray absorption coefficient is obtained from the partial projection image data and a panoramic X-ray image is produced.

The local region to obtain the panoramic X-ray image of the dental arch is located around the center of the curved sectional area, namely at the axis of symmetry of the dental arch and also an appropriate position between the cervical vertebrae and the dental arch. Such an area is advantageous because it has little obstacle.

The formulas used for the X-ray CT for producing a panoramic X-ray image are almost the same, however, a little consideration is required for an integration range, a filter function for backprojection, and a filter function used for an X-ray projection data.

Figure 27A:
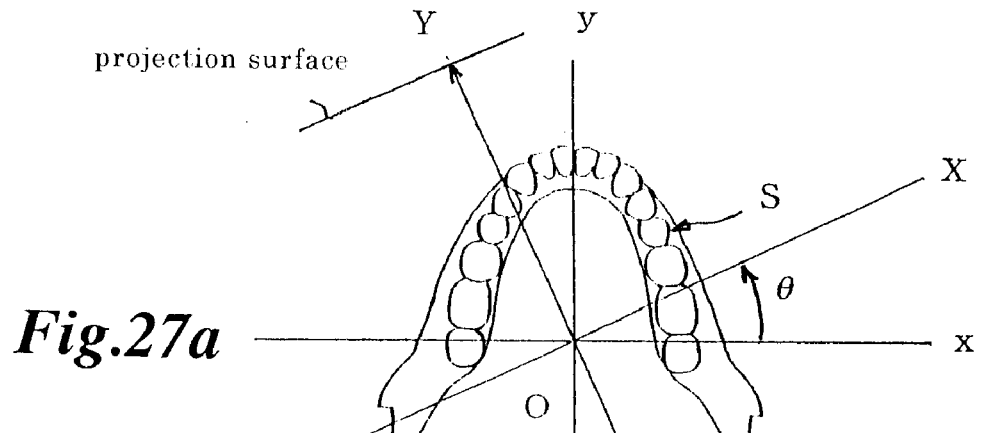
FIG. 27a and FIG. 27b explain the fundamental principle of an X-ray CT method for producing a panoramic X-ray image according to the present invention.

According to the method, the centers of xOy coordinate and XOY coordinate become the center of the local region and become the center of the curved sectional area when an orthodox projected panoramic X-ray image of the dental arch is produced. Here such an example is explained. FIG. 27a explains such a projection method and FIG. 27b explains an integration range.

The (formula 9) and (formula 10) in FIG. 33 used in this method are the same as the (formula 5) and (formula 6) in FIG. 32 for the above-mentioned X-ray CT method. However, the value of "2r" is the beam width in rotary direction of an ortho-conical X-ray beam, not a conical X-ray beam.

The qs $(X,\theta)$ is a backprojection data from the partial X-ray projection image data by an actually projected ortho-conical X-ray beam. The qn $(X,\theta)$ is a backprojection data from the X-ray projection image data by the X-ray beam bundle which hasn't been actually radiated but exists in the conventional X-ray CT method.

According to the method, because the irradiation area of the ortho-conical X-ray beam is limited, only qs$(X,\theta)$ relating to rects (X) is actually obtained, thereby qn$(X,\theta)$=0. Therefore, backprojection is executed using qs$(X,\theta)$ and (formula 11) is derived from (formula 10).

According to a normal X-ray CT method of the present invention, the integration range of $\theta$ is $[0, 2\pi]$ or $[0,\pi]$ when fs(x, y) is obtained. The integration range is further limited in this method.

Figure 27B:
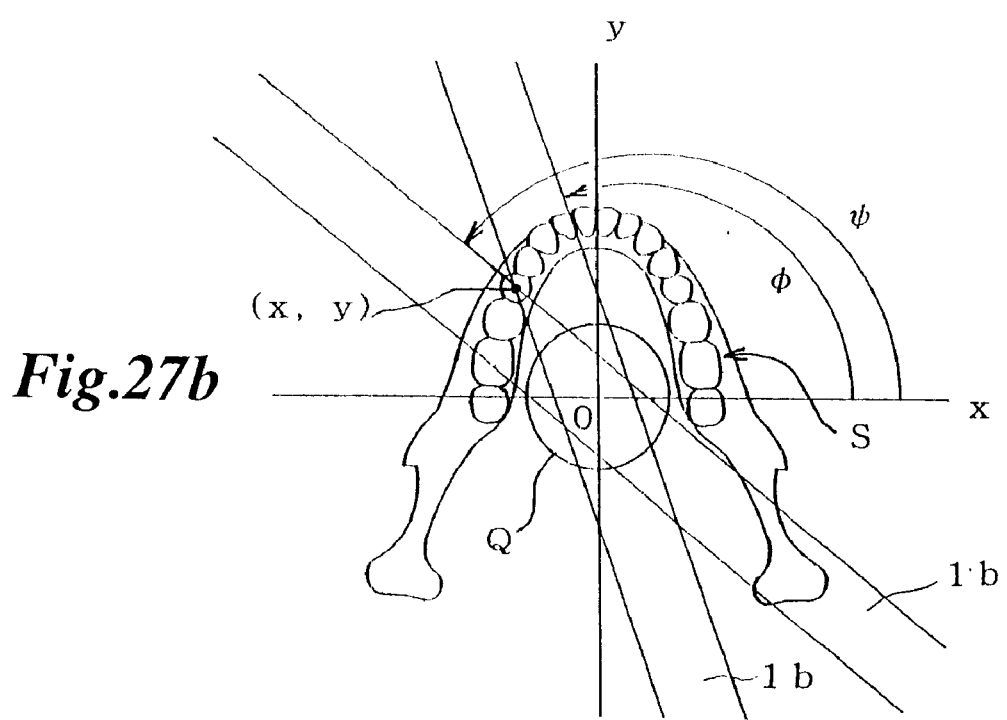

FIG. 27b shows the integration range. As shown in the figure, the integration range of this method is, when the point (x, y) of the dental arch S is considered, from the angle $\phi(x, y)$ starting projection of the ortho-conical X-ray beam on the point (x, y) to the angle $\Psi(x, y)$ finishing projection.

The meaning of the starting and finishing angle is that they are design value for calculation and the value smaller than the angle which the ortho-conical X-ray beam actually irradiates the point (x, y), namely an optional integration range from the angle $\phi(x, y)$ to the angle $\Psi(x, y)$, can be selected.

Because the angle $\phi(x, y)$ and the angle $\Psi(x, y)$ can be determined as design values at an optional point of the dental arch, they become the function of x and y.

Using the angle $\phi(x, y)$ and the angle $\Psi(x, y)$, the backprojection formula of the present invention is shown in (formula 12) in FIG. 33.

Figure 28A:
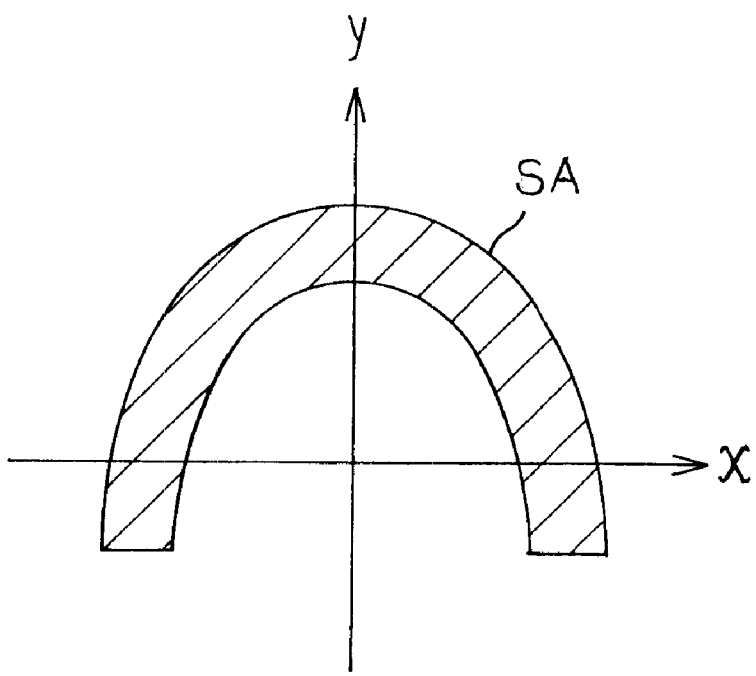
FIG. 28a and FIG. 28b explain the fundamental principle of an X-ray CT method for producing a panoramic X-ray image according to the present invention.
Figure 28B:
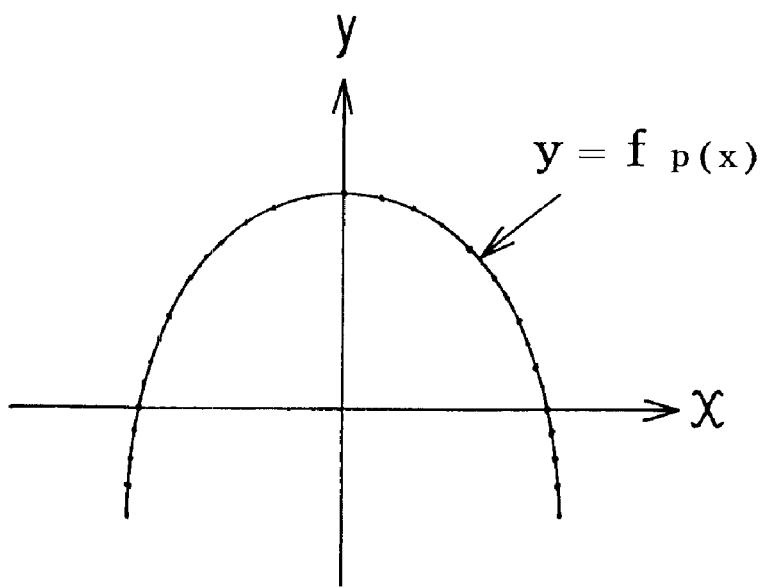

The range for calculating fs(x, y) of the (formula 12) may be the required range of the curved sectional area SA shown in FIG. 28a. The panoramic sectional image of the dental arch represented by the formula, y=fp(x), is determined in advance as shown in FIG. 28b and fs(x, y) of the (formula 12) may be calculated only about the point (x, fp(x)) on the surface.

Artifact Measure

Next an artifact measure for an artifact caused by operating the fs(x, y) will be described. The artifact is, also called a false image, a discordance of data produced where the values of the conditional expressions are rapidly changed in an image processing. Following artifact measure may be taken in order to eliminate such an artifact.

Artifact Measure

As the terminal of the above-mentioned conditional functions rects(X) is rapidly changed from 0 to 1, an artifact is apt to be caused by the point on the beam passing the point (x, y) at the angle $\phi(x, y)$ and the angle $\Psi(x, y)$ at which the conical X-ray beam starts or finishes radiating. The filter function changing more smoothly at the terminal is preferably used for calculating the (formula 10) instead of rects(X) to eliminate the artifact.

Following Hamming function, Hanning function or Blackman function may be used for the filter function.

Hamming function:
Hamming $(\tau, X)=0.54-0.46*\cos(2\pi*X/2\tau)$

Hanning function:
Hanning $(\tau, X)=0.5*(1.0-\cos(2\pi*X/2\tau)$

Blackman function:
Blackman $(\tau, X)=0.42-0.5*\cos(2\pi*X/2\tau)+0.08*\cos(4\pi*X/2\tau)$ These functions are used for excluding the artifact at both terminals at the relation in FIG. 29a.

The functions aren't limited in the above-mentioned and any function of which terminals smoothly approach "0" may be used.

In the above formula, "*" indicates multiplication.

<Artifact Measure 2>

Another artifact element, which is generated at starting and finishing of the conical X-ray beam irradiation as shown in FIG. 29b can be considered. The filter function the same as the above artifact measure 1 can be used for such an element.

INDUSTRIAL APPLICABILITY

According to the X-ray CT method of the present invention, it isn't required for producing a panoramic X-ray image to turn the rotary arm following a complicated loci to form an envelope curve as in the prior art. In the present invention, radiographing is performed with the center of rotation fixed at the center of a specific region. Therefore, the construction of the apparatus can be almost the same as that of the partial X-ray CT method and its construction can be availably used.

Further, a conical X-ray beam is locally radiated only on the specific region of the curved sectional area so as to radiograph by turning onece under 360° so that the apparatus can be downsized. Moreover comparing with the conventional prior X-ray CT method, a radiograph time is remarkably reduced and the X-ray exposed dose is decreased to about 1 to 5% of that in case of using conventional systems.

In the present invention, the three-dimensional distribution information of an X-ray absorption coefficient obtained for the curved sectional area is reconstructed and the panoramic X-ray image is obtained, the affect of an obstacle bone, a crown and an implant is rarely received.

The apparatus can be constructed as a vertical type X-ray CT apparatus for rotary radiating an X-ray vertically for a standing or sitting patient so that such a compact type X-ray CT apparatus is suitable for a dental clinic in which installing area is small.

Furthermore according to this method, because a panoramic X-ray image overlapping images seen from a projection line intersecting at a specified angle to a panoramic image layer for producing the panoramic X-ray image is obtained, foreign object hidden if seen from one direction can be easily found, and because diverse sectional images are obtained by changing a direction of the projection line for the same sectional image layer, how a tooth is overlapped with another can be more acculately recognized. In case of producing panoramic X-ray images, the panoramic image layer seen from different directions of projection line for the same sectional image layer can be provided as mentioned above so that the method of the present invention is highly useful for diagnosis.

According to tie X-ray CT method described in a first embodiment, the specified angle of the projection line and the normal line of the panoramic image layer in the method of a first embodiment is set at 0 (zero) degree. The three-dimensional distribution information of an X-ray absorption coefficient for the once obtained curved sectional area by local radiation is reconstructed while presetting a direction of the normal line for the panoramic image layer as a direction of a projection line, is used for producing a panoramic X-ray image, thereby a panoramic X-ray image suitable for diagnosing the cavities of adjacent teeth being obtained.

According to the X-ray CT method described in a second embodiment, in addition to the effects of the first embodiment, an operational method is defined to be a weighted average. According to the weighted average, experimentally obtained weighing can be done for each data in case of calculating a three-dimensional distribution information so that more accurate panoramic X-ray image can be obtained.

According to the X-ray CT method described in a third embodiment, in addition to the effects of the first or second embodiment, the specified angle is defined as an angle in which the direction of the projection line is a direction of the normal line for the rising direction of tooth. Therefore, if front teeth are inclined for the panoramic image layer, their curate images can be obtained and accurate diagnosis can be made.

According to the X-ray CT method described in a fourth embodiment, in addition to the effect of the first embodiment, it is clear that the specified angle isn't limited to be two-dimensional and is a three-dimensional angle including an up and down direction and/or a right and left direction for the panoramic image layer. When the rising direction and the overlapping direction of teeth are three-dimensionally inclined such as an up and down direction and/or a right and left direction, this method can be suitably applied.

According to the X-ray CT method described in a fifth embodiment, in addition to the effects of the first or fourth embodiments, the specified angle is set to be equal for any regions of the panoramic image layer so that panoramic X-ray images seen from a direction of the projection line inclining at an equal angle for any regions of the panoramic image layer are obtained and are sensuously understood.

According to the X-ray CT method described in a sixth embodiment, in addition to the effects of the first, fourth or fifth embodiments, a setting method of the specified angle for determining a direction of the projection line is defined so that such a setting method can be easily executed.

According to the X-ray CT method described in a seventh embodiment, in addition to the effects of the first through sixth embodiments, a method for conforming the rotating center of the rotary arm and the center of the specified region can be selected from two ways according to the object to be moved so that these are plural choices for conforming those centers.

According to the X-ray CT method described in an eight embodiment, in addition to the effects of the first through seventh embodiments, radiating beam is an ortho-conical X-ray beam from the first instead of extracting a partial X-ray projection image information presumably obtained by an ortho-conical X-ray beams from the X-ray projection image information after radiating conical X-ray beams. Therefore, the exposed dose to the object to be examined can be more reduced.

According to the X-ray CT method described in a ninth embodiment, in addition to the effects of the first through eighth embodiments, conical X-ray beams are radiated on the object while the rotary arm is turned with the axial direction of the rotating axis of the rotary arm inclining at a specified angle for a perpendicular direction of the object or the rotary arm is turned with the object inclining at a specified angle for the axial direction of the rotating arm of the rotary arm. Therefore, conical X-ray beams can be radiated in a direction so as not to transmit a cervix which becomes an affecting shadow and the affect of the shade can be reduced. In the latter method, the apparatus can be simplified because the direction of the object, which doesn't rotate, is incline.

According to the X-ray CT method described in a tenth embodiment, in addition to the effects of the first trough eighth embodiments, X-rays are radiated on the object while the rotary arm is turned while making the rotary axis a given precession movement, namely grinding movement, so that conical X-ray beams can avoid the affecting shadow which can't be avoided if they are radiated horizontally.

The X-ray CT apparatus in an eleventh embodiment is to achieve the CT method of and have the same effect as that of the second embodiment.

The X-ray CT apparatus in a twelveth embodiment is to achieve the CT method of and have the same effect as that of the third embodiment.

The X-ray CT apparatus in a thirteenth embodiment is to achieve the CT method of and have the same effect as that of the fourth embodiment.

The X-ray CT apparatus in a fourteenth embodiment is to achieve the CT method of and have the same effect as that of the fifth embodiment.

The X-ray CT apparatus in a fifteenth embodiment is to achieve the CT method of and have the same effect as that of the sixth embodiment.

The X-ray CT apparats in a sixteenth embodiment is to achieve the CT method of and have the same effect as that of the seventh embodiment.

The X-ray CT apparatus in a seventeenth embodiment is to achieve the CT method of and have the same effect as that of the eighth embodiment.

The X-ray CT apparatus in an eighteenth embodiment is to achieve the CT method of and have the same effect as that of the ninth embodiment.

The X-ray CT apparatus in a nineteenth embodiment is to achieve the CT method of and have the same effect as that of the tenth embodiment.

The X-ray CT apparatus in a twentieth embodiment is, in addition to the effects of the eleventh to nineteenth embodiments, the curved section area is one of a local region where a few teeth are rising, a temporomandibular joint region or an otorhinolaryngologic region. In this case, panoramic X-ray images seen from optical projection lines can be obtained for these regions in a same manner.

The X-ray CT apparatus in a twenty-first embodiment is, in addition to the effects of the eleventh to twentieth embodiments, provided with display means capable of sequentially displaying the panoramic X-ray image obtained while changing the specified angle by means of the angle setting means. Therefore, the images in which a specified angle is seen from varied directions can be obtained according to diagnosis purposes so that such an apparatus has a high diagnosis value.

According to the X-ray CT apparatus in a twenty-second embodiment, in addition to the effect of the twenty-first embodiment, the display means of the twenty-first embodiment is defined to display panoramic X-ray images while continuously changing the direction of the projection line so that it has high diagnosis value.

According to the X-ray CT apparatus in a twenty-third embodiment, in addition to the effect of the twenty-first embodiment, the CT method of the twelveth embodiment is separately used for the curved sectional areas of the upper jaw and the lower jaw and the display means of the twenty-first embodiment is defined to display one combined panoramic X-ray image of thus obtained panoramic X-ray image of the upper jaw and thus obtained panoramic X-ray image of the lower jaw. Therefore, images corresponding to each rising direction of teeth can be obtained so that such images have high diagnosis value.

According to the X-ray CT apparatus in a twenty-fourth embodiment, in addition to the effects of the twenty-first to twenty-third embodiments, as plural panoramic X-ray images can be selected and displayed in array on the same screen, displaying image can be selected according to diagnosis purposes, thereby achieving convenience.

According to the X-ray CT apparatus in a twenty-fifth embodiment, in addition to the effect of the twenty-fourth embodiment, the display means of the twenty-fourth embodiment is defined to display in array the panoramic X-ray images seen from an optional direction of the projection line and the panoramic X-ray images seen from the normal line, same as the prior art. Such an apparatus is useful for comparing and judging the images.

According to the X-ray CT apparatus in a twenty-sixth embodiment, in addition to the effects of the eleventh to twenty-fifth embodiments, at least one of functions same as operated in the apparatuses of the eleventh to twenty-fifth embodiment can be selectively operated. Therefore, several kinds of panoramic X-ray images can be obtained and shown by one apparatus so that it is useful for diagnosis.

What is claimed is:

1. An X-ray computed tomography method, comprising:
   sequentially obtaining on a two-dimensional X-ray image sensor an X-ray projection image information of a curved sectional area by photographing with a rotary am tuning while locally radiating conical X-ray beams constantly passing through only a specific region from an X-ray generator, conforming a rotating center of the rotary arm and a center of the specific region in the curved sectional area along a dental arch, which is an object to be examined, or inside of a bow-shape of the curved sectional area, said rotary am including the X-ray generator and the two-dimensional X-ray image sensor facing to each other;
   arithmetically processing thus obtained X-ray projection image information by a backprojection method and computing a three-dimensional distribution information of an X-ray absorption coefficient of said curved sectional area; and
   calculating said three-dimensional distribution information of X-ray absorption coefficient on a projection line intersecting a normal line of a panoramic image layer at a specified angle for any regions of the panoramic image layer of said curved sectional area and obtaining a panoramic X-ray image of said curved sectional area seen from said projection line by expanding the calculated result on a two-dimensional plane.

2. An X-ray computed tomography method, comprising:
   sequentially obtaining on a two-dimensional X-ray image sensor an X-ray projection image information of a curved sectional area by photographing with a rotary arm turning while locally radiating conical X-ray beams constantly passing through only a specific region from an X-ray generator, conforming a rotating center of the rotary arm and a center of the specific region in the curved sectional area along a dental arch, which is an object to be examined, or inside of a bow-shape of the curved sectional area, said rotary arm including the X-ray generator and the two-dimensional X-ray image sensor facing to each other;
   arithmetically processing thus obtained X-ray projection image information by a backprojection method and computing a three dimensional distribution information of an X-ray absorption coefficient of said curved sectional area; and
   calculating said three-dimensional distribution information of an X-ray absorption coefficient on a projection line for any regions of the panoramic image layer of said curved sectional area, presetting a normal line of the panoramic image layer as the projection line, and obtaining a panoramic X-ray image of said curved sectional area seen from said projection line by expanding the calculated result on a two-dimensional plane.

3. The X-ray computed tomography method as set forth in claims 1 or 2 wherein a calculated result of a weighted average of said three-dimensional distribution information of an X-ray absorption coefficient on said projection line is expanded on a two-dimensional plane so as to obtain a panoramic X-ray image from said three-dimensional distribution information of an X-ray absorption coefficient of said curved sectional area.

4. The X-ray computed tomography method as set forth in claim 1 wherein a direction of said projection line farther becomes a direction of a normal line for a rising direction of each tooth constituting the dental arch corresponding to said curved sectional area.

5. The X-ray computed tomography method as set forth in claim 1 wherein said specified angle is constructed to be adjustable at an optional angle in up and down direction and/or right and left direction for said panoramic image layer.

6. The X-ray computed tomography method as set forth in claims 1 or 5 wherein said specified angle is constructed so as to be equal for any regions of said panoramic image layer.

7. The X-ray computed tomography method as set forth in claim 1 wherein either said specified angle is infinitely and variably adjustable or it is selectable from plural specified angles.

8. The X-ray computed tomography method as set forth in claim 1 wherein said object to be examined is moved for said rotating center of the rotary arm or said rotating center of the rotary arm is moved for said object to be examined for positioning so as to conform said rotating center of the rotary arm and said center of the specific region.

9. The X-ray computed tomography method as set forth in claim 1 wherein only ortho-conical X-ray beams which is approximately perpendicular to said panoramic image layer are extracted from said conical X-ray beams and are radiated, a partial X-ray projection image information obtained on said two-dimensional X-ray image sensor by the ortho-conical X-ray beams is arithmetically processed by a backprojection method and the three-dimensional distribution information of an X-ray absorption coefficient of said curved sectional area is obtained, and a panoramic X-ray image is obtained by expanding the three-dimensional distribution information on a two-dimensional plane.

10. The X-ray computed tomography method as set forth in claim 1 wherein X-rays are radiated on an object to be examined while said rotary arm is turned with an axial direction of said rotating axis of said rotary arm inclining at a specified angle for a perpendicular direction of said object or said rotary arm is turned with said object inclining at a specified angle for the axial direction of said rotating arm of said rotary arm.

11. The X-ray computed tomography method as set forth in claim 1 wherein X-rays are radiated on said object to be examined while said rotary arm is turned while making said rotating axis a given precession movement.

12. An X-ray computed tomography apparatus, comprising:
   a rotary arm with an X-ray generator and a two-dimensional image sensor faced to each other;
   position adjusting means for conforming a rotating center of said rotary arm and a center of a specific region in a curved sectional area along a dental arch, which is an object to be examined, or inside of a bow-shape of the curved sectional area;
   turning means for turning said rotary arm while locally radiating conical X-ray beams constantly passing through only the specific region from said X-ray generator;
   image storage means for sequentially storing an X-ray projection image information of said curved sectional area obtained on said two-dimensional X-ray image sensor by said X-ray conical beams;
   arithmetic processing means for calculating thus obtained X-ray projection image information by a backprojection method and computing a three-dimensional distribution information of an X-ray absorption coefficient of said curved sectional area; and
   angle setting means for setting a specified angle of a normal line of a panoramic image layer in said curved sectional area and a projection line intersecting the normal line; wherein
      said arithmetic processing means calculates the three-dimensional distribution information of the X-ray absorption coefficient on the projection line intersecting at the specified angle set by said angle setting means for any regions on said panoramic image layer, the calculated result is expanded on a two-dimensional plane, and a panoramic X-ray image of said curved sectional area seen from a direction of said projection line is obtained.

13. An X-ray computed tomography apparatus, comprising:
   a rotary arm with an X-ray generator and a two-dimensional image sensor faced to each other;
   position adjusting means for conforming a rotating center of said rotary arm and a center of a specific region in a curved sectional area along a dental arch, which is an object to be examined, or inside of a bow-shape of the curved sectional area,
   turning means for turning said rotary arm while locally radiating conical X-ray beams constantly passing through only the specific region from said X-ray generator;
   image storage means for sequentially storing an X-ray projection image information of said curved sectional area obtained on said two-dimensional X-ray image sensor by said conical X-ray beams;
   arithmetic processing means for calculating thus obtained X-ray projection image information by a backprojection method and computing a three-dimensional distribution information of an X-ray absorption coefficient of said curved sectional area; and
   angle setting means for setting a specified angle of a normal line of a panoramic image layer in said curved sectional area and a projection line intersecting the normal line; wherein
      said angle setting means sets said specified angle in such a manner that a direction of said projection line conforms to a direction of said normal line of said panoramic image layer for any regions on said panoramic image layer of said curved sectional area, said arithmetic processing means calculates the three-dimensional distribution information of the X-ray absorption coefficient on said projection line for said regions, the calculated result is expanded on a two-dimensional plane, and a panoramic X-ray image of said curved sectional area seen from a direction of said projection line is obtained.

14. The X-ray computed tomography apparatus as set forth in claims 12 or 13 wherein said arithmetic processing means expands a calculated result of a weighted average of said three-dimensional distribution information of the X-ray absorption coefficient on said projection line on the two-dimensional plane so as to obtain a panoramic X-ray image from the three-dimensional distribution information of the X-ray absorption coefficient of said curved sectional area.

15. The X-ray computed tomography apparatus as set forth in claim 12 wherein said angle setting means is further constructed in such a manner that a direction of said projection line also becomes a direction of a normal line for a rising direction of each tooth constituting the dental arch corresponding to said curved sectional area.

16. The X-ray computed tomography apparatus as set forth in claim 12 wherein said angle setting means is constructed in such a manner that said specified angle is adjustable at an optional angle in up and down direction and/or right and left direction for said panoramic image layer.

17. The X-ray computed tomography apparatus as set forth in claim 12 wherein said angle setting means is constructed in such a manner that said specified angle is equal for any regions of said curved sectional area.

18. The X-ray computed tomography apparatus as set forth in claim 12 wherein said angle setting means is comprised of variable means for infinitely and variably adjusting said specified angle and/or selection means for selecting said specified angle from predetermined plural angles.

19. The X-ray computed tomography apparatus as set forth in claim 12 wherein said position adjusting means is constructed in such a manner that said object to be examined is moved for said rotating center of said rotary arm or said rotating center of said rotary arm is moved for said object to be examined for positioning so as to conform said rotating center of said rotary arm and said center of said specific region.

20. The X-ray computed tomography apparatus as set forth in claim 12, further comprising X-ray beam width restriction means for extracting and radiating only ortho-conical X-ray beams which arc approximately perpendicular to said panoramic image layer from said conical X-ray beams, and wherein said arithmetic processing means arithmetically processes a partial X-ray projection image information obtained on said two-dimensional X-ray image sensor by the ortho-conical X-ray beams by a backprojection method and the three-dimensional distribution information of the X-ray absorption coefficient of said curved sectional area is obtained, and a panoramic X-ray image is obtained by expanding thus obtained three-dimensional distribution information on the two-dimensional plane.

21. The X-ray computed tomography apparatus as set forth in claim 12 wherein X-rays are radiated on the object to be examined while said rotary arm is turned with the axial direction of said rotating axis of said rotary arm inclining at a specified angle for a perpendicular direction of the object by providing rotating axis direction setting means capable of inclining the axial direction of said rotating axis of said rotary arm or X-rays are radiated on the objected to be examined while said rotary arm is turned with the object inclining at a specified angle for the axial direction of said rotating center of said rotary arm by providing object supporting direction setting means capable of inclining the object's supporting direction.

22. The X-ray computed tomography apparatus as set forth in claim 12 wherein said turning means is constructed in such a manner that said rotary arm is turned while making said rotating axis of said rotary arm a given precession movement.

23. The X-ray computed tomography apparatus as set forth in claim 12 wherein said curved sectional area is any one of a local region where a few teeth are rising, a temporomandibular joint region or an otorhinolaryngologic region.

24. The X-ray computed tomography apparatus as set forth in claim 12, further comprising displaying means capable of sequentially displaying said panoramic X-ray image obtained while setting said specified angle by means of said angle setting means.

25. The X-ray computed tomography apparatus as set forth in claim 24 wherein said display means can sequentially show said panoramic X-ray image obtained while continuously changing said specified angle by means of said variable means of said angle setting means as set forth in claim 18.

26. The X-ray computed tomography apparatus as set forth in claim 24 wherein said display means can combine a panoramic X-ray image of an upper jaw and a panoramic X-ray image of a lower jaw, both obtained by the apparatus as set forth in claim 15, into one panoramic X-ray image for displaying, said panoramic X-ray image of the upper jaw being obtained by setting a normal line direction for a rising direction of a tooth of a curved sectional area along the upper jaw as a projection line and said panoramic image of the lower jaw being obtained by setting a normal line direction for a rising direction of a tooth of a curved sectional area along the lower jaw.

27. The X-ray computed tomography apparatus as set forth in claim 24 wherein said display means can select plural panoramic X-ray images obtained under different conditions and display in array on the same screen.

28. The X-ray computed tomography apparatus as set forth in claim 27 wherein said display means can display said panoramic X-ray image obtained in claim 12 and said panoramic X-ray image obtained in claim 13 in array on the same screen, said panoramic X-ray image obtained in claim 12 being seen from said projection line intersecting said normal line of said panoramic image layer at a specified angle and said panoramic X-ray image obtained in claim 13 being seen from said projection line by setting said normal line of said panoramic image layer as said projection line.

29. The X-ray computed tomography apparatus wherein at least one of functions same as operated in the apparatuses as set forth in any one of claims 12, 13 and 15 to 27 can be selectively operated.

* * * * *